US006723349B1

(12) United States Patent
Hill et al.

(10) Patent No.: US 6,723,349 B1
(45) Date of Patent: *Apr. 20, 2004

(54) POLYOXOMETALATE MATERIALS, METAL-CONTAINING MATERIALS, AND METHODS OF USE THEREOF

(75) Inventors: Craig L. Hill, Atlanta, GA (US); Ling Xu, Atlanta, GA (US); Jeffrey T. Rhule, Franklin, OH (US); Eric A. Boring, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/689,231

(22) Filed: Oct. 11, 2000

Related U.S. Application Data (60) Provisional application No. 60/158,952, filed on Oct. 12, 1999.

(51) Int. Cl.$^7$ ............................. A61K 9/06; A61K 9/10; A61K 9/00; A61K 33/00; A61K 33/06; A61K 33/24; A61K 33/42; A01N 59/16; A01N 59/26; A61L 9/00; A62D 3/00

(52) U.S. Cl. ...................... 424/604; 424/601; 424/602; 424/603; 424/605; 424/606; 424/617; 424/646; 424/682; 424/691; 424/59; 424/76.21; 424/402; 424/405; 424/411; 424/414; 424/443; 424/484; 424/DIG. 13; 514/823; 514/844; 514/845; 514/848; 514/862; 514/887; 514/937; 514/944; 514/969; 514/974; 588/200; 588/205; 422/5

(58) Field of Search ......................... 424/59, 600–606, 424/DIG. 13, 617, 646, 682, 691, 76.21, 402, 405, 411, 414, 443, 484; 514/844, 845, 848, 887, 974, 823, 862, 937, 944, 969; 422/5; 588/200, 205

(56) References Cited

U.S. PATENT DOCUMENTS

| | | | | |
|---|---|---|---|---|
| 4,639,432 A | | 1/1987 | Holt et al. | 502/324 |
| 4,870,010 A | | 9/1989 | Hayes | 424/114 |
| 5,071,877 A | | 12/1991 | Bannard et al. | 514/640 |
| 5,093,134 A | * | 3/1992 | Murrer et al. | 424/617 |
| 5,292,558 A | | 3/1994 | Heller et al. | 427/533 |
| 5,356,469 A | | 10/1994 | Jenkins et al. | 106/404 |
| 5,607,979 A | | 3/1997 | McCreery | 514/759 |
| 5,824,706 A | * | 10/1998 | Schinazi et al. | 514/492 |
| 5,851,948 A | | 12/1998 | Chuang et al. | 502/314 |
| 5,908,647 A | | 6/1999 | Golightly et al. | 426/74 |
| 5,914,436 A | | 6/1999 | Klabunde et al. | 588/205 |
| 5,928,382 A | | 7/1999 | Reinhardt et al. | 8/111 |
| 5,990,373 A | | 11/1999 | Klabunde | 588/205 |
| 6,020,369 A | * | 2/2000 | Schinazi et al. | 514/492 |
| 6,057,488 A | | 5/2000 | Koper et al. | 588/200 |
| 6,224,885 B1 | | 5/2001 | Jenner et al. | 424/401 |
| 6,410,603 B1 | * | 6/2002 | Hobson et al. | 514/759 |
| 6,414,039 B1 | * | 7/2002 | Braue, Jr. et al. | 514/759 |
| 6,420,434 B1 | | 7/2002 | Braue, Jr. et al. | 514/759 |
| 2003/0216256 A1 | * | 11/2003 | Axtell et al. | 502/417 |
| 2003/0220195 A1 | * | 11/2003 | Axtell et al. | 502/417 |

FOREIGN PATENT DOCUMENTS

| | | |
|---|---|---|
| DE | 3001657 A1 | 11/1981 |
| DE | 300641 A | 6/1992 |
| EP | 242296 A | 10/1987 |
| EP | 271337 A | 6/1988 |
| EP | 426124 A2 | 5/1991 |
| GB | 1385489 * | 2/1975 |
| JP | 4054127 A | 2/1992 |
| JP | 08296031 | 11/1996 |
| SU | 1783323 A | 12/1992 |
| WO | WO 9203511 A | 3/1992 |
| WO | WO 97/14401 | 4/1997 |
| WO | WO99/53131 | 10/1999 |

OTHER PUBLICATIONS

Chemical Abstracts 131:234039 (1999).*
Chemical Abstracts 128:27274 (1997).*
Gall et al., "Selective Oxidation of Thioether Mustard (HD) Analogs by tert–Butylhydroperoxide Catalyzed by $H_5PV_2Mo_{10}O_{40}$ Supported on Porous Carbon Materials", Journal of Catalysis 159, 473–478 (1996).
Gall et al., "Role of Water in Polyoxometalate–Catalyzed Oxidations in Nonaqueous Media. Scope, Kinetics, and Mechanism of Oxidation of Thioether Mustard (HD) Analogs tert–Butyl Hydroperoxide Catalyzed by $H_5PV_2Mo_{10}O_{40}$", Inorg. Chem. 1994, 33, pp. 5015–5021, 1994.

(List continued on next page.)

Primary Examiner—John Pak
(74) Attorney, Agent, or Firm—Thomas, Kayden, Horstemeyer & Risley, LLP

(57) ABSTRACT

The invention relates to a polyoxometalate topical composition for removing a contaminant from an environment, comprising a topical carrier and at least one polyoxometalate, with the proviso that the polyoxometalate is not $H_5PV_2Mo_{10}O_{40}$; $K_5Si(H_2O)Mn^{III}W_{11}O_{39}$; $K_4Si(H_2O)Mn^{IV}W_{11}O_{39}$; or $K_5Co^{III}W_{12}O_{40}$. The invention further relates to a method for removing a contaminant from an environment, comprising contacting the polyoxometalate topical composition of the present invention with the environment containing the contaminant for a sufficient time to remove the contaminant from the environment. The invention further relates to a modified polyoxometalate, wherein the modified polyoxometalate comprises the admixture of (1) a polyoxometalate and (2) a cerium compound, a silver compound, a gold compound, a platinum compound, or a combination thereof. The invention further relates to a method for removing a contaminant from an environment, comprising contacting a modified material with the environment containing the contaminant for a sufficient time to remove the contaminant from the environment, wherein the modified material comprises (1) a material and (2) a metal compound comprising a transition metal compound, an actinide compound, a lanthanide compound, or a combination thereof, wherein the metal compound is not a polyoxometalate. The invention further relates to an article comprising the modified material of the present invention.

17 Claims, 2 Drawing Sheets

OTHER PUBLICATIONS

Hulea et al., "Thioether Oxidation by Hydrogen Peroxide Using Titanium–Containing Zeolites As Catalysts", Journal of Molecular Catalysis A: Chemical 111, 325–332, (1996).

Walmsley, "Synthesis of A Heteropolytungstate and Its Use in Outer–Sphere Redox Kinetics", Journal of Chemical Education, vol. 69, No. 11, 936–938 (1992).

Harrup et al., "Polyoxometalate Catalysis of the Aerobic Oxidation of Hydrogen Sulfide to Sulfur", Inorg. Chem., 33, 5448–5455 (1994).

Hill et al., "The First Combinatorially Prepared And Evaluated Inorganic Catalysts. Polyometates For The Aerobic Oxidation of The Mustard Analog Tetrahydrothiophene (THT)", Journal of Molecular Catalysis A: Chemical 114, pp. 103–111, (1996).

Riley et al., "Selective Molecular Oxygen Oxidation of Thioethers to Sulfoxides Catalyzed by Ce(IV)", Journ. American Chemical Society, 110, pp. 177–180 (1988).

Zeng et al., "Catalytically Decontaminating Dendrimers. Poly–Tris Arborols Covalently Funcationalized With Redox Active Polyoxomeatalates", Proc. Erdec Sci. Conf. Chem. Biol. Def. Res., pp. 351–357, Nov. 1997.

Johnson et al., "CW–Agent Detecting Barrier Creams" Emory Department of Chemistry, Proc. Erdec Sci. Conf. Chem. Biol. Def. Res. pp. 393–399, Nov. 1997.

Rhule et al., "New Polyoxometalate–TSPS for CW Agent Detection and Decontamination", Proc. Erdec Sci. Conf. Chem. Biol. Def. Res. pp. 307–313, Nov. 1998.

Gall et al., Carbon Powder and Fiber–Supported Polyoxometalate Catalytic Materials. Preparation, Characterization, and Catalytic Oxidation of Dialkyl Sulfides as Mustard (HD) Analogues), Chemistry of Materials, vol. 8, No. 10, pp. 2523–2527 (1996).

Katsoulis, "A Survey of Applications of Polyoxometalates", Chem Rev., 98, pp. 359–387 (1998).

* cited by examiner

POLYOXOMETALATE MATERIALS, METAL-CONTAINING MATERIALS, AND METHODS OF USE THEREOF

CROSS REFERENCE TO RELATED APPLICATIONS

This application claims priority upon U.S. provisional application serial No. 60/158,952, filed on Oct. 12, 1999, and the contents of which are herein incorporated by this reference in their entirety.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Grant No.s: DAMD17-99-C-9012 and DAAG55-98-1-0251 awarded by the Army/MRMC.

FIELD OF THE INVENTION

The present invention relates to materials containing a polyoxometalate or a metal compound, wherein the metal compound is not a polyoxometalate. The invention further relates to methods for removing a contaminant from an environment by contacting the environment with a polyoxometalate material or a non-polyoxometalate material.

BACKGROUND OF THE INVENTION

Decreasing the potential danger of contaminants from the environment has long been a significant issue. For example, the removal of offensive odors originating from cigarette smoke, sweat, exhaust gases, and rotten food in the work place, the home, and elsewhere would be quite beneficial to the public-at-large. Additionally, materials that can remove highly toxic contaminants, such as chemical warfare agents (CWAs), from the environment can ultimately reduce a soldier's exposure to the agent. Examples of materials that would be useful include creams, powders, coatings, and fabrics.

Creams, also referred to as topical skin protectants (TSPs), have been developed to protect soldiers from the threat of dermal exposure to chemical warfare agents. TSPs require an inert material which can be applied on the skin in a thin layer to form an antipenetrant barrier to CWAs or other contact irritants that will not interfere excessively with normal skin functions. A preferred TSP affords protection against CWAs and other toxic or irritating materials in all of the forms in which they might be encountered (e.g., liquid, aerosolized liquid and vapor). Perhaps the best-known vesicant CWA is 2,2'-dichlorodiethylsulfide (also known as "HD" or "sulfur mustard"), which was first used during World War I. Improved TSPs, however, are needed for protecting military personnel and civilians from percutaneous exposure to CWAs and protecting the skin from contact dermatitis arising from other sources as well.

U.S. Pat. No. 5,607,979 to McCreery discloses topical creams formed from about 35% to about 50% fine particulates of certain poly(tetrafluoroethylene) (PTFE) resins dispersed in perfluorinated polyether oils having viscosities from about 20 cSt to about 350 cSt. The creams afford protection against chemical warfare agents such as sulfur mustard (HD), lewisite (L), sulfur mustard/Lewisite mixtures (HL), pinacolyl methylphosphonofluoridate (soman or GD), thickened soman (TGD), and O-ethyl-S-2-diisopropylaminoethyl methylpholsphosponothiolate (VX). These creams, however, can only provide limited exposure to a CWA for a short period of time. Furthermore, the creams cannot convert the CWA to an inactive form, which will reduce the overall toxicity of the CWA.

Thus, there is a need for a material, which is also referred to herein as a support, that can remove a contaminant from the environment for an extended period of time. The incorporation of a polyoxometalate (herein referred to as "POM") into a material such as a cream, coating, powder, or fabric, is one approach to removing a contaminant from an environment. Gall et al. (*Chem. Mat.* 8, pp. 2523–2527, 1996) disclose the immobilization of $H_5PV_2Mo_{10}O_{40}$ on carbon cloth in order to determine the ability of $H_5PV_2Mo_{10}O_{40}$ to remove sulfur containing compounds from toluene. Johnson et al. (*Proc. ERDEC Sci. Conf. Chem. Biol. Def. Res.*, 1998, pp. 393–399) disclose suspending $H_5PV_2Mo_{10}O_{40}$; $K_5Si(H_2O)Mn^{III}W_{11}O_{39}$; $K_4Si(H_2O)Mn^{IV}W_{11}O_{39}$; or $K_5Co^{III}W_{12}O_{40}$ in a perflouropolyether barrier cream to determine the creams ability to detect the presence of mustard gas. Johnson et al., however, is not concerned with the removal of the mustard gas from the gas phase.

The prior art also discloses the incorporation of polyoxometalates into powders and coatings. For example, U.S. Pat. No. 5,356,469 to Curcio et al. disclose a metal pigment composition suitable for the formation of a coating composition. The coating composition is composed of a solvent, a metal pigment, at least one phosplhosilicate pigment, and at least one heteropoly anion. The metal pigment particles possess increased stability against attack by water. Japanese patent application number 4054127 to Terumo Corp. discloses the use of heteropoly acid salts as anti-tumor agents. The heteropoly acid salts call be administered in the form of a powder or suspended in solution. Although the prior art discloses a number of different applications of polyoxometalate powders or coatings, the art does not disclose the use of a powder or coating containing a polyoxometalate to remove a contaminant from the environment.

In light of the above, it would be very desirable to have an article and a method of using an article for the removal of toxic and/or malodorous compounds without adding stoichiometric amounts of additives or compounds to the article. The present invention solves such a need in the art while providing surprising advantages. The present invention herein incorporates a polyoxometalate (POM) into a material such as a topical carrier, powder, or coating, which greatly increases the ability of the to remove a contaminant from the environment. The present invention also incorporates a metal compound, wherein the metal compound is not a polyoxometalate, into a in order to remove a contaminant from the environment.

SUMMARY OF THE INVENTION

In accordance with the purpose(s) of this invention, as embodied and broadly described herein, this invention, in one aspect, relates to a polyoxometalate topical composition for removing a contaminant from an environment, comprising a topical carrier and at least one polyoxometalate, with the proviso that the polyoxometalate is not $H_5PV_2Mo_{10}O_{40}$; $K_5Si(H_2O)Mn^{III}W_{11}O_{39}$; $K_4Si(H_2O)Mn^{IV}W_{11}O_{39}$; or $K_5Co^{III}W_{12}O_{40}$.

The invention further relates to a method for removing a contaminant from an environment, comprising contacting the polyoxometalate topical composition of the present invention with the environment containing the contaminant for a sufficient time to remove the contaminant from the environment.

The invention further relates to a method for removing a contaminant from an environment, comprising contacting a polyoxometalate powder or a polyoxometalate coating with the environment containing the contaminant for a sufficient time to remove the contaminant from the environment.

The invention further relates to a modified polyoxometalate, wherein the modified polyoxometalate comprises the admixture of (1) a polyoxometalate and (2) a cerium compound, a silver compound, a gold compound, a platinum compound, or a combination thereof.

The invention further relates to a method for removing a contaminant from an environment, comprising contacting a modified material with the environment containing the contaminant for a sufficient time to remove the contaminant from the environment, wherein the modified material comprises (1) a material and (2) a metal compound comprising a transition metal compound, an actinide compound, a lanthanide compound, or a combination thereof, wherein the metal compound is not a polyoxometalate.

The invention further relates to a modified material for removing a contaminant from an environment, wherein the modified material comprises (1) a material comprising a topical carrier, a powder, a coating, or a fabric, and (2) a metal compound comprising a transition metal compound, an actinide compound, a lanthanide compound, or a combination thereof, wherein the metal compound is not a polyoxometalate.

The invention further relates to an article comprising the modified of the present invention.

Additional advantages of the invention will be set forth in part in the description which follows, and in part will be obvious from the description, or may be learned by practice of the invention. The advantages of the invention will be realized and attained by means of the elements and combinations. It is to be understood that both the foregoing general description and the following detailed description are exemplary and explanatory only and are not restrictive of the invention.

DETAILED DESCRIPTION OF THE INVENTION

The present invention may be understood more readily by reference to the following detailed description of preferred embodiments of the invention and the Examples included therein.

Before the present methods and articles are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

In accordance with the purpose(s) of this invention, as embodied and broadly described herein, this invention, in one aspect, relates to a polyoxometalate topical composition for removing a contaminant from an environment, comprising a topical carrier and at least one polyoxometalate, with the proviso that the polyoxometalate is not $H_5PV_2Mo_{10}O_{40}$; $K_5Si(H_2O)Mn^{III}W_{11}O_{39}$; $K_4Si(H_2O)Mn^{IV}W_{11}O_{39}$; or $K_5Co^{III}W_{12}O_{40}$.

The invention further relates to a modified polyoxometalate, wherein the modified polyoxometalate comprises the admixture of (1) a polyoxometalate and (2) a cerium compound, a silver compound, a gold compound, a platinum compound, or a combination thereof.

The invention further relates to a modified material for removing a contaminant from an environment, wherein the modified material comprises (1) a material comprising a topical carrier, a powder, a coating, or a fabric, and (2) a metal compound comprising a transition metal compound, an actinide compound, a lanthanide compound, or a combination thereof, wherein the metal compound is not a polyoxometalate.

The invention further relates to an article comprising the modified material of the present invention.

Many polyoxometalates known in the art can be used in the present invention to remove a contaminant from an environment. Polyoxometalates are also referred to in the art as heteropoly compounds, heteropoly acids, isopoly compounds, and isopoly acids, which are subsets of polyoxometalates. Examples of polyoxometalates useful in the present invention are disclosed in Pope, M. T. in *Heteropoly and Isopoly Oxometalates*, Springer Verlag, 1983, and *Chemical Reviews*, vol. 98, No. 1, pp. 1–389, 1998, which are incorporated by this reference in their entirety.

The selection of the polyoxometalate used in the present invention is dependent upon the contaminant or contaminants to be removed from the environment. In one embodiment, the polyoxometalate has the formula 1 of $[V_kMo_mW_nNb_oTa_pM_qX_rO_s]y^-[A]$, wherein M is at least one f-block element or d-block element having at least one d-electron, wherein M is not vanadium, molybdenum, tungsten, niobium, or tantalum; X is at least one p-, d-, or f-block element, wherein X is not oxygen; k is from 0 to 30; m is from 0 to 160; n is from 0 to 160; o is from 0 to 10; p is from 0 to 10; q is from 0 to 30; r is from 0 to 30; s is sufficiently large that y is greater than zero; and y is greater than zero, wherein the sum of k, m, n, o, and p is greater than or equal to four; and the sum of k, m, and q is greater than zero, and A is one or more different counterions. In one embodiment, s is from 19 to 460. The charge on the POM, y, is dictated by the values of k, m, n, o, p, q, r and s. The p-, d-, and f-block elements can exist in any oxidation state.

Generally, M can be any d-block element having at least one d-electron or f-block element having at least one f-electron. Typically, M comprises titanium, chromium manganese, cobalt, iron, nickel, copper, rhodium, silver, palladium, platinum, mercury, ruthenium, cerium, or europium In a preferred embodiment, M comprises manganese, cobalt, or ruthenium. In another embodiment, X comprises phosphorus, silicon, aluminum boron, cobalt, zinc, or iron. When the polyoxometalate has the Keggin structure $XM_{12}$, then it is possible for X and at least one M to be the same d- or f-block element. Not wishing to be bound by theory, it is believed that the metal ion M of the polyoxometalate of the present invention is responsible for removing the contaminant from the gas phase, while X, when present, provides structural integrity to the polyoxometalate.

In one embodiment, the sum of k and q is greater than or equal to one, the sum of k, m, n, o, p, and q is 12, and s is 40. In yet another embodiment, k is not zero. In another embodiment, q is not zero.

In a more specific embodiment, when the polyoxometalate has the formula 1, the polyoxometalate has the formula $[X^{g+}V_b{}^{j+}M_c{}^{h+}Z_{12-b-c}{}^{i+}O_x]^{u-}[A]$, wherein X is at least one p-, d-, or f-block element; g is greater than or equal to 2; M is at least one f-block element or -block element having at least one d-electron, wherein M is no vanadium h is from 1 to 7; i is from 5 to 6; j is from 4 to 5; x is 39 or 40; Z is tungsten, molybdenum, niobium, or a combination thereof, b is from 0 to 6; c is from 0 to 6; u is from 3 to 9; and A is a counterion. The values of u, x, i, b, c, g, h, and j will vary depending upon the selection of X, M, and Z. The variables are related to one another and can be derived by the following formula:

$$u = 2(x) - i(12-b-c) - g - c(h) - b(j)$$

The values of h, i, and j are average charges, and depend upon the selection and number of X, M, Z, and V present in the POM. For example, when Z is $Nb^{+5}$ and $Nb^{+6}$ (i.e., two Nb atoms present in the POM), the value of i+ is 5.5.

In a more specific embodiment, when the polyoxometalate has the formula 1, the polyoxometalate has the formula $[X^{g+}V_b{}^{j+}Z_{12-b}{}^{i+}O_{40}]^{u-}[A]$, wherein X is at least one phosphorus, silicon, aluminum, boron, zinc, cobalt, or iron; b is from 1 to 6, and u is from 3 to 9.

In a more specific embodiment, when the polyoxometalate has the formula 1, the polyoxometalate has the structure $[X^{g+}M_c{}^{h+}Z_{12-c}{}^{i+}O_{40}]^{u-}[A]$, wherein X is at least one phosphorus, silicon, aluminum, boron, zinc, cobalt, or iron; c is from 1 to 6, and u is from 3 to 9.

In a more specific embodiment, when the polyoxometalate has the formula 1, the polyoxometalate has the formula $[X_2{}^{r+}V_u{}^{s+}M_v{}^{t+}Z_{18-u-v}{}^{y+}O_z]^{w-}[A]$, wherein X is at least one p-, d-, or f-block element; r is greater than or equal to 1; M is at least one f-block element or d-block element having at least one d-electron, wherein M is not vanadium; t is from 1 to 7; s is from 4 to 5; Z is tungsten, molybdenum, niobium, or a combination thereof; u is from 0 to 9; v is from 0 to 9; y is from 5 to 6; z is 61 or 62; w is greater than or equal to 4; and A is a counterion. Similar to the formula above, the values of r, s, t, u, v, w, y, and z, will vary depending upon the selection of X, M, and Z. The variables are related to one another and can be derived by the following formula:

$$w = 2(z) - y(18-u-v) - 2r - v(t) - u(s)$$

The values of r, s, t, and y are also average charges, and depend upon the selection and number of X, M, Z, and V atoms present in the POM.

In a more specific embodiment, when the polyoxometalate has the formula 1, the polyoxometalate has the formula $[X_2{}^{r+}V_u{}^{s+}Z_{18-u}{}^{y+}O_{62}]^{w-}[A]$, wherein X is at least one phosphorus, sulfur, silicon, aluminum, boron, zinc, cobalt, or iron; u is from 1 to 9; and w is greater than or equal to 4.

In a more specific embodiment, when the polyoxometalate has the formula 1, the polyoxometalate has the formula $[X_2{}^{r+}M_v{}^{t+}Z_{18-v}{}^{y+}O_{62}]^{w-}[A]$, wherein X is at least one phosphorus, sulfur, silicon, aluminum, boron, zinc, cobalt, or iron; v is from 1 to 9; and w is greater than or equal to 4.

In a more specific embodiment, when the polyoxometalate has the formula 1, the polyoxometalate has the formula $[YV_pZ_{12-p}O_{40}][A]$, wherein Y is phosphorus, silicon, or aluminum; Z is tungsten or molybdenum; p is from 1 to 6, and A is a counterion. In one embodiment, Y is phosphorus and Z is molybdenum In one embodiment, Y is phosphorus and Z is tungsten. In one embodiment, Y is silicon and Z is molybdenum. In one embodiment, Y is silicon and Z is tungsten. In one embodiment, Y is aluminum and Z is tungsten. In one embodiment, Y is aluminum and Z is molybdenum.

In a more specific embodiment, when the polyoxometalate has the formula 1, the polyoxometalate has the formula $[X^{g+}V_bM^{h+}{}_cZ_{12-b-c}O_{40}]^{u-}[A]$, wherein X is at least one p-, d-, or f-block element; g+ is the charge of X; M is at least one f-block element or d-block element having at least one d-electron, wherein M is not vanadium; h+ is the charge of M; Z is tungsten, molybdenum, niobium, or a combination thereof; b is from 0 to 6; c is from 0 to 6, wherein the sum of b and c is greater than or equal to one; u is greater than 3; and A is a counterion.

In a more specific embodiment, when the polyoxometalate has the formula 1, the polyoxometalate has the formula $[X^{g+}V_bZ_{12-b}O_{40}]^{u-}[A]$, wherein X is at least one phosphorus, silicon, aluminum, boron, zinc, cobalt, or iron; Z comprises tungsten, molybdenum, niobium, or a combination thereof; b is from 1 to 6; and u is greater than 3.

In a more specific embodiment, when the polyoxometalate has the formula 1, the polyoxometalate has the formula $[X^{g+}M^{h+}{}_cZ_{12-c}O_{40}]^{u-}[A]$, wherein X is at least phosphorus, silicon, aluminum, boron, zinc, cobalt, or iron; Z comprises tungsten, molybdenum, niobium, or a combination thereof; $M^{h+}$ is at least one f-block element or d-block element having at least one d-electron; c is from 1 to 6; and u is greater than 3.

In a more specific embodiment, when the polyoxometalate has the formula 1, the polyoxometalate has the formula $[X^{i+}{}_2V_uM^{j+}{}_vZ_{18-u-v}O_{62}]^{w-}[A]$, wherein X is at least one p-, d-, or f-block element; i+ is the charge of X; M is at least one d- or f-block element, wherein M is not vanadium; j+ is the charge of M; Z is tungsten, molybdenum, niobium, or a combination thereof; u is from 0 to 9; v is from 0 to 9, wherein the sum of u and v is greater than or equal to one; w is greater than or equal to 4; and A is a counterion.

In a more specific embodiment, when the polyoxometalate has the formula 1, the polyoxometalate has the formula $[X^{i+}{}_2V_uZ_{18-u}O_{62}]^{w-}[A]$, wherein X is at least one phosphorus, sulfur, silicon, aluminum, boron, zinc, cobalt, or iron; Z comprises tungsten, molybdenum, niobium, or a combination thereof; u is from 1 to 9; and w is greater than or equal to 4.

In a more specific embodiment, when the polyoxometalate has the formula 1, the polyoxometalate has the formula $[X^{i+}{}_2M^{j+}{}_vZ_{18-v}O_{62}]^{w-}[A]$, wherein X is at least one phosphorus, sulfur, silicon, aluminum, boron, zinc, cobalt, or iron; Z comprises tungsten, molybdenum, niobium, or a combination thereof; $M^{j+}$ is at least one d- or f-block element; v is from 1 to 9; and w is greater than or equal to 4.

In a more specific embodiment, when the polyoxometalate has the formula 1, the polyoxometalate has the formula $[YV_xZ_{12-x}O_{40}][A]$, wherein Y is phosphorus, silicon, or aluminum; Z is tungsten or molybdenum; x is from 1 to 6, and A is a counterion. In one embodiment, Y is phosphorus and Z is molybdenum. In one embodiment, Y is phosphorus and Z is tungsten. In one embodiment, Y is silicon and Z is molybdenum. In one embodiment, Y is silicon and Z is tungsten. In one embodiment, Y is aluminum and Z is tungsten. In one embodiment, Y is aluminum and Z is molybdenum.

Polyoxometalates having an organic group, such as an alkyl group or aryl group, an organosilyl group, or other p- or d-block organometallic groups bonded to the POM can also be used in the present invention. The organic group can be branched or straight chain alkyl, alkenyl, or alkynyl group or an aryl group of $C_1$ to $C_{30}$. The alkyl group can also be a polyether or polyol. Not wishing to be bound by theory, the organic group is bonded to the polyoxometalate as depicted in Scheme 1, where R is the organic group and Met is generally vanadium, molybdenum, tungsten, niobium, or tantalum:

Scheme I

The reaction between an alcohol and the polyoxometalate I results in the loss of water and the formation of the polyoxometalate II, wherein the organic group is bonded to an oxygen atom of the polyoxometalate. Any alcohol known in the art can be used in the present invention. Examples of alcohols that can be used include, but are not limited to, methanol, ethanol, or tris(hydroxymethyl)methane. The polyoxometalates having organic groups bonded to the POM that are disclosed in Gouzerh et al., *Chem. Rev.*, 98, pp. 77–111, 1998, which is incorporated by reference in its entirety, are useful in the present invention.

In another embodiment, the polyoxometalate I can be reacted with a compound having the generic formula $YL_oR_{4-o}$, wherein Y is silicon, tin, or an other p- or d-block element; L is a leaving group; R is an organic group, such as an alkyl, alkenyl, or alkynyl group or an aryl group of $C_1$ to $C_{30}$; and o is from 1 to 4. Suitable leaving groups for L include, but are not limited to, halides and alkoxides. In Scheme I, the oxygen of polyoxometalate I displaces L from $YLR_3$ to form a new Y—O bond (compound III). Any silyl, tin, or organic derivative of a p- or d-block element known in the art can be used in the present invention, provided that the compound has at least one leaving group.

The counterion A can be any counterion known in the art. Examples of counterions include, but are not limited to, quaternary ammonium cation, proton, alkali metal cation, alkaline earth metal cation, ammonium cation, d-block cations, f-block cations, or a combination thereof. In one embodiment, the polyoxometalate is an acid, wherein the counterion A is hydrogen ($H^+$). In one embodiment, the counterion is a d- or f-block metal complex. In one embodiment, the counterion is trimethyl-triazacyclononane manganese. In another embodiment, the counterion A is hydrogen, lithium ($Li^+$), sodium ($Na^+$), potassium ($K^+$), or a combination thereof. In another embodiment, A is not hydrogen or potassium.

In another embodiment, the polyoxometalate comprises a modified polyoxometalate, wherein the modified polyoxometalate comprises the admixture of (1) a pre-modified polyoxometalate and (2) a cerium compound, a silver compound, a gold compound, a platinum compound, a copper compound, a cobalt compound, or a combination thereof. The term "admixture" can refer to the reaction product between the polyoxometalate and the cerium compound, silver compound, gold compound, platinum compound, or a combination thereof. For example, the cerium compound, silver compound, gold compound, or platinum compound can undergo ion exchange with the counterion of the polyoxometalate. The cerium compound, silver compound, gold compound, or platinum compound can also react with the polyoxometalate by a redox reaction. The term "admixture" can also refer to when the cerium compound, silver compound, gold compound, or platinum compound do not react at all with the polyoxometalate. For example, the polyoxometalate may absorb the cerium compound, silver compound, gold compound, or platinum compound.

In one embodiment, when the POM is the sodium, lithium, or potassium salt or the acid form (A is $H^+$), the POM can undergo ion exchange with a cerium compound, a silver compound, a gold compound, a platinum compound, or a combination thereof. For example, $Ag_5PV_2Mo_{10}O_{40}$ is produced by the ion exchange of $Na_5PV_2Mo_{10}O_{40}$, with a stoichiometric amount $AgNO_3$. Any of the POMs described above can undergo ion exchange with a cerium compound, a silver compound, a gold compound, a platinum compound.

Depending upon the type and amounts of POM and cerium compound, silver compound, gold compound, or platinum compound used, the ion exchange reaction may or may not go to completion. When the ion exchange does not go to completion, there may be small population of $Na^+$, $Li^+$, $K^+$, or $H^+$ in the modified-polyoxometalate. For example, when $H_5PV_2Mo_{10}O_{40}$ is admixed with $AgNO_3$, the resultant POM may be expressed by the formula $Ag_xH_{5-x}PV_2Mo_{10}O_{40}$ where x is from 1 to 5. Here, varying amounts of $H^+$ may be present in the POM.

An example of a cerium compound useful in the present invention includes, but is not limited to, $(NH_4)_2Ce(NO_3)_6$. Examples of silver compounds useful in the present invention include, but are not limited to, $AgNO_3$ and $AgClO_4$. Examples of gold compounds useful in the present invention include, but are not limited to, $HAuCl_4$ and salts thereof. An example of a platinum compound useful in the present invention includes, but is not limited to, $H_2PtCl_6$.

In one embodiment, the counterion is cerium, silver, gold, platinum, or a combination thereof: In another embodiment, A is, independently, cerium, silver, gold, or platinum In another embodiment, A is (1) cerium and silver; (2) cerium and platinum; (3) cerium and gold; or (4) silver and gold.

In another embodiment, A comprises (1) hydrogen, lithium sodium, potassium, or a combination thereof; and (2) cerium, silver, gold, platinum or a combination thereof.

In one embodiment, (1) the pre-modified polyoxometalate is $H_5PV_2Mo_{10}O_{40}$; $Na_5PV_2Mo_{10}O_{40}$; $Li_5PV_2Mo_{10}O_{40}$; $K_5PV_2Mo_{10}O_{40}$, or a combination thereof, and (2) the cerium compound is $(NH_4)_2Ce(NO_3)_6$. In another embodiment, (1) the pre-modified polyoxometalate is $H_5PV_2Mo_{10}O_{40}$; $Na_5PV_2Mo_{10}O_{40}$; $Li_5PV_2Mo_{10}O_{40}$; $K_5PV_2Mo_{10}O_{40}$, or a combination thereof; (2) the cerium compound is $(NH_4)_2Ce(NO_3)_6$; and (3) the gold compound is $HAuCl_4$. In another embodiment, (1) the pre-modified polyoxometalate is $H_5PV_2Mo_{10}O_{40}$; $Na_5PV_2Mo_{10}O_{40}$; $Li_5PV_2Mo_{10}O_{40}$; $K_5PV_2Mo_{10}O_{40}$, thereof; (2) the cerium compound is $(NH_4)_2Ce(NO_3)_6$; and (3) the platinum compound is $H_2PtCl_6$. In another embodiment, (1) the pre-modified polyoxometalate comprises $Na_4PVMo_{11}O_{40}$; $Na_5PV_2Mo_{10}O_{40}$; $Na_6PV_3MO_9O_{40}$; $Na_5H_2PV_4W_8O_{40}$; $Na_9PV_6Mo_6O_{40}$; $Na_5CuPW_{11}O_{39}$; $Na_5CuPW_{11}O_{39}$; $Na_5MnPW_{11}O_{39}$; $K_5CoPW_{11}O_{39}$; $(n-Dec_4)_6$ HMnNb$_3$P$_2$W$_{15}$O$_{62}$; or K$_{12}$Cu$_3$(W$_9$PO$_{34}$)$_2$, and (2) the gold compound is HAuCl$_4$. In another embodiment, (1) the pre-modified polyoxometalate is Na$_5$PV$_2$Mo$_{10}$O$_{40}$ and (2) the silver compound is AgNO$_3$, AgClO$_4$ or a combination thereof.

In another embodiment, the polyoxometalate comprises K$_8$Co$_2$W$_{11}$O$_{39}$; K$_8$SiCoVW$_{10}$O$_{39}$; K$_7$SiCoVW$_{10}$O$_{39}$; Na$_8$Co$_2$W$_{11}$O$_{39}$; Ag$_5$PV$_2$Mo$_{10}$O$_{40}$; Ag$_6$PV$_3$Mo$_9$O$_{40}$; Ag$_8$CoVW$_{11}$O$_{40}$; Ag$_{12}$Ce(PW$_{11}$O$_{39}$)$_2$; Na$_{12}$Ce(PW$_{11}$O$_{39}$)$_2$; K$_{12}$Ce(PW$_{11}$O$_{39}$)$_2$; Na$_5$PCuW$_{11}$O$_{39}$; H$_6$PV$_3$Mo$_9$O$_{40}$; or K$_5$CU$^{II}$PW$_{11}$O$_{39}$. In another embodiment, the polyoxometalate is not H$_6$PV$_3$Mo$_9$O$_{40}$.

Not wishing to be bound by theory, it is believed that some counterions of the present invention can be reduced to the corresponding metal when the polyoxometalate contacts the contaminant. For example, when the cation is Ag$^{+1}$ or Au$^{+3}$, these cations can be reduced to silver metal or Au$^{+1}$, respectively, depending upon the contaminant that is to be removed. Thus, the counterion A call exist in multiple valence states.

The phrase "metal compound" refers to one or more transition metal compounds, actinide compounds, lanthanide compounds, or a combination thereof. When the metal compound is only one compound, then the material is directly treated with the metal compound using techniques described below. When the metal compound is composed of two or more compounds, the material can be sequentially treated with the compounds, or alternatively, the metal compounds can be admixed prior to treating the material with the metal compounds. Depending upon the metal compounds that are selected, the metal compounds may react with one another to form a new species, or they may not react at all with each other to produce a composition or mixture. Materials that contain a metal compound of the present invention are referred to herein as "non-POM materials."

In one embodiment, the metal compound comprises a cerium compound, a gold compound, a platinum compound, a silver compound, or a combination thereof. Any of the cerium compounds, gold compounds, platinum compounds, or silver compounds listed above can be used as the metal compound. In another embodiment, the metal compound is a cerium compound and a platinum compound, preferably (NH$_4$)$_2$Ce(NO$_3$)$_6$ and H$_2$PtCl$_6$, respectively. In another embodiment, the metal compound is a cerium compound and a gold compound, preferably (NH$_4$)$_2$Ce(NO$_3$)$_6$ and HAuCl$_4$, respectively. In another embodiment, the metal compound is a silver compound and a gold compound, preferably AgNO$_3$ and/or AgClO$_4$ and HAuCl$_4$, respectively. In another embodiment, the metal compound is a cerium compounds, preferably (NH$_4$)$_2$Ce(NO$_3$)$_6$.

In another embodiment, the metal compound comprises (1) gold, copper, and nitrate; (2) gold, iron, and nitrate; (3) gold, manganese, and nitrate; (4) gold, titanium, and nitrate; (5) gold, cobalt, and nitrate; (6) gold and nitrate; (7) copper and nitrate; (8) iron and nitrate; (9) gold, vanadium, and nitrate; (10) gold, nickel, and nitrate; (11) gold, silver, and nitrate; or (12) gold, chloride, and nitrate. In a preferred embodiment, the metal compound comprises gold, chloride, and nitrate. In another embodiment, the metal compound comprises mixing (NEt$_4$)AuCl$_2$ with varying amounts of CuSO$_4$, MnSO$_4$, VOSO$_4$, Ti(SO$_4$)$_2$, Fe$_2$(SO$_4$)$_3$, NiSO$_4$, ZnSO$_4$, Cr$_2$(SO$_4$)$_3$, MgSO$_4$, CoSO$_4$, Pd(NO$_3$)$_4$, Na$_2$SO$_3$, and/or NBu$_4$NO$_3$. In another embodiment, the metal compound is produced by mixing (NEt$_4$)AuBr$_2$ and NBu$_4$NO$_2$.

When the metal compound comprises two or more compounds, the compounds can be admixed using techniques known in the art. In one embodiment, the metal compound can be produced by admixing two or more metal salts. The anion of the salt can be any anion known in the art. Examples of anions include, but are not limited to, sulfate, carbonate, acetate, nitrate, chloride, and stearate. In one embodiment, when two or more compounds are used to produce the metal compound, the compounds are mixed in the presence of a solvent, preferably an organic solvent. In one embodiment, After the compounds have been sufficiently admixed, the solvent is removed, and the metal compound is optionally dried. In one embodiment, the drying step is by vacuum.

Any POM or metal compound of the present invention can be incorporated into a material in order to remove a contaminant from the environment. Examples of materials include, but are not limited to, a topical carrier, a coatings a powder, or a fabric. As described above, a material as used herein refers to a support that holds the POM or metal compound.

In one embodiment, the polyoxometalate and the metal compound can be incorporated sequentially into the material. In one embodiment, the polyoxometalate is incorporated into the material followed by the incorporation of the metal compound into the material. In another embodiment, the metal compound is incorporated into the material followed by the incorporation of the polyoxometalate into the material.

A wide variety of topical carriers can be used in the present invention. Suitable topically acceptable pharmaceutical carriers are those which typically are used in the topical application of pharmaceuticals and cosmetics. Examples of such carriers include, but are not limited to, lotions, creams, ointments, and gels. Topical carriers are also referred to in the art as barrier cream and topical skin protectants. Any of the topical carriers disclosed in U.S. Pat. No. 5,607,979 to McCreery can be used in the present invention, which is incorporated by reference in its entirety. In one embodiment, the topical carrier comprises a perfluorinated polymer. In another embodiment, the topical carrier comprises a perfluoropolyether. An example of a perfluoropolyether (PFPE) useful in the present invention has the general formula CF$_3$O[—CF(CF$_3$)CF$_2$O—]$_x$(—CF$_2$O—)$_y$CF$_3$). In one embodiment, the topical carrier comprises a perfluorinated polymer and one or more unfluorinated polymers. In another embodiment, the topical carrier comprises a perfluoropolyether and one or more unfluorinated polyethers.

In one embodiment, the topical carrier may further contain saturated or unsaturated fatty acids such as stearic acid, palmitic acid, oleic acid, palmito-oleic acid, cetyl or oleyl alcohols, stearic acid, fluorinated acids, fluorinated alcohols (e.g., tetrafluoroethanol), or combinations thereof. The cream may also optionally contain one or more surfactants, such as a non-ionic surfactant.

In one embodiment, the polyoxometalate topical composition is composed of a perfluoropolyether and the counterion A of the POM is silver. In another embodiment, the polyoxometalate topical composition is composed of a perfluoropolyether and the metal compound is a silver compound, a gold compound, or a combination thereof in another embodiment, the non-POM material comprises a topical carrier composed of a perfluoropolyether and the metal compound comprises a silver compound, preferably AgNO$_3$ or AgClO$_4$.

In another embodiment, the non-POM topical composition is composed a perfluoropolyether and the metal compound comprises a cerium compound, a silver compound, a palladium compound, a platinum compound, or a silver compound.

A wide variety of powders and coatings known in the art can be used as the material of the present invention. In one embodiment, the powder comprises activated carbon.

Any fabric known in the art can be used to produce a polyoxometalate fabric or non-POM fabric of the present invention. In one embodiment, fabrics used to prepare garments, draperies, carpets, and upholstery can be used and articles made from them are a part of this invention. In another embodiment, the fabric can be a knit or non-woven fabric. Useful fibers include, but are not limited to, polyamide, cotton, polyacrylic, polyacrylonitrile, polyester, polyvinylidine, polyolefin, polyurethane, polytetrafluoroethylene, or carbon cloth, or a combination thereof: In one embodiment, the fabric is prepared from cotton, polyacrylic, or polyacrylonitrile. In one embodiment, the fabric is prepared from a cationic fiber. In another embodiment, the fabric comprises (1) a 50/50 blend of nylon-6,6 and cotton or (2) stretchable carbon blended with polyurethane.

Any cellulosic fiber can be incorporated by a POM or metal compound to produce the polyoxometalate fibers or non-POM fibers of the present invention. Examples of useful cellulosic fibers include, but are not limited to, wood or paper. In a preferred embodiment, a polyoxometalate or the metal compound of the present invention can be incorporated in paper in order to remove a contaminant from the gas or liquid phase. In one embodiment, the paper is wallpaper.

The amount of polyoxometalate or metal compound incorporated into the material varies depending upon the contaminant to be removed and the material that is selected. There is no restriction on the amount of POM or metal compound that call be incorporated into the material. In one embodiment, the amount of polyoxometalate or metal compound incorporated in the material is from 0.1 to 95% by weight of the polyoxometalate material or non-POM material. In one embodiment, the lower limit of polyoxometalate or metal compound by weight is 0.1, 0.5, 1.0, 2.0, 5.0, 10, 15, 20, 25, 30, 35, 40, 45, or 50%, and the upper limit is 30, 40, 50, 60, 70, 80, 90, or 95%. In one embodiment, when the material is a topical carrier, the polyoxometalate or metal compound is from 5 to 30% by weight of topical composition.

The present invention is capable of removing a single contaminant or multiple contaminants from an environment. The term "environment" as used herein refers to any media that contains at least one contaminant. In one embodiment, the environment comprises a liquid phase. In another embodiment, the environment comprises a gas phase.

The term "remove" refers to, but is not limited to, the degradation of the contaminant, the conversion of the contaminant into another compound that is either less toxic or nontoxic and/or malodorous, or the adsorption of the contaminant by the polyoxometalate or the metal compound. The POM and metal compound can degrade the contaminant by a number of different mechanisms. For example, the POM call aerobically oxidize the contaminant acetaldehyde ($CH_3CHO$). Not wishing to be bound by theory, it is believed that the aerobic oxidation of $CH_3CHO$ proceeds by a radical chain mechanism (i.e., the initiation of the radical chain by $CH_3CHO+POM_{ox} \rightarrow CH_3CO.+HPOM_{red}$).

Contaminants that can be removed by using the present invention include, but are not limited to, an aldehyde, an aliphatic nitrogen compound, a sulfur compound, an aliphatic oxygenated compound, a halogenated compound, all organophosphate compound, a phosphonothioate compound, a phosphonothioate compound, an arsenic compound, a chloroethyl-amine compound, a phosgene compound, a cyanic compound, or a combination thereof. In one embodiment, the contaminant is acetaldehyde, methyl mercaptan, ammonia, hydrogen sulfide, methyl sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, or a combination thereof. In another embodiment, the polyoxometalate materials and non-polyoxometalate materials can remove microbial life from the gas or liquid phase. Examples of microbial life include, but are not limited to, bacteria, protozoa, and viruses.

In another embodiment, the contaminant is a chemical warfare agent (CWA). The chemical warfare agents disclosed in Marrs, Timothy C.; Maynard, Robert. L; Sidell, Frederick R.; *Chemical Warfare Agents Toxicology and Treatment*; John Wiley & Sons: Chichester, England, 1996; Compton, James A. F. *Military Chemical and Biological Agents Chemical and Toxicological Properties*; The Telford Press: Caldwell, N.J., 1988; Somani, Satu M. *Chemical Warfare Agents*; Academic Press: San Diego, 1992, which are herein incorporated by reference in their entirety, can be removed by the polyoxometalate materials of the present invention.

The present invention can remove a contaminant from the environment in the gas phase under mild conditions. In one embodiment, the contaminant can be removed from −50° C. to 250° C. at a pressure of from 0.1 ppb to 30 atm, preferably from 25° C. to 105° C. at 1 atm In another embodiment, the lower temperature limit is −50, −40, −30, −20, −10, 0, 10, 20, 50, 75, 100, or 150° C., and the upper temperature limit is 50, 75, 100, 125, 150, 175, 200, 225, or 250° C. In a preferred embodiment, the present invention can remove a contaminant from the environment at room temperature (approximately 25° C.) and at I atm. In another embodiment, the present invention can remove a contaminant from the gas phase that has a partial pressure of from 0.1 ppb to 2 atm, 10 ppb to 2 atm, 100 ppb to 2 atm, 200 ppb to 2 atm, and 0.5 ppm to 2 atm Similarly, the present invention can remove a contaminant under mild conditions when the environment is a liquid phase. In one embodiment, the contaminant call be removed from a liquid media at from 0° C. to 200° C. The temperature depends upon the liquid media that is being contacted and the contaminant to be removed.

The POMs and metal compounds are typically used in the presence of an oxidizer to remove a contaminant from the environment. In one embodiment, the POMs and/or metal compounds are used in the presence of air, which oxidizes the POM and/or metal compound. In another embodiment, additional oxidizers can be used in combination with air to oxidize the POM and/or metal compound. Examples of oxidizers include, but are not limited to, peroxides and peracids. In a preferred embodiment, air is used as the oxidizer.

The environment containing the contaminant can be contacted by the polyoxometalate materials or non-POM materials using a variety of techniques. For example, when the contaminant is in the liquid phase, the polyoxometalate material or non-POM material can be dipped or submersed into the liquid phase. Alternatively, the liquid phase can be filtered or passed through the polyoxometalate material or non-POM material. When the contaminant is in the gas phase, the polyoxometalate material or non-POM material is typically placed in an open or closed environment that contains the contaminant(s).

The polyoxometalate materials or non-POM materials of the present invention have a number of advantages over the prior art materials that do not use a polyoxometalate to remove a contaminant from the environment. One advantage is that the present invention can remove a contaminant from the environment starting within milliseconds of contact and can remove the contaminant for extended periods of time, ranging from several days to indefinitely. The POMs and metal compounds used in the present invention are capable of being regenerated to an active form that permits the removal of the contaminant. Another advantage is that some POMs and metal compounds can render the material more water resistant and increase the surface area of the material. Finally, when the material is a fabric or cellulosic fiber, the POM and metal compound can enhance the dyeability, light fastness, color fastness, and weaving properties of the fabric or cellulosic fiber.

The polyoxometalate and metal compound can be incorporated into the material using techniques known in the art. In one embodiment, when the material is a topical carrier, powder, or coating, the polyoxometalate or metal compound is directly added to and admixed with the material. In another embodiment, the material (topical carrier, powder, coating, or fabric) is contacted with a mixture comprising the polyoxometalate or metal compound and a solvent. The polyoxometalate or metal compound can be soluble, partially soluble, or insoluble in the solvent, depending upon the polyoxometalate or metal compound and solvent selected. In one embodiment, the solvent is water. In another embodiment, the solvent can be an organic solvent. Examples of organic solvents useful in the present invention include, but are not limited to, acetonitrile, acetone, toluene, carbon dioxide, xylenes, 1-methyl-2-pyrrolidinone, dimethyl sulfoxide, or an alcohol, such as methanol, ethanol, 1-propanol, or 2-propanol.

In one embodiment, when the material is a fabric or cellulosic fiber, the polyoxometalate or metal compound mixture is from 0.1 to 20% by weight polyoxometalate or metal compound and from 80 to 99.9% by weight water, preferably from 0.3 to 15% by weight polyoxometalate or metal compound and 85 to 99.7% water. Generally, the fabric or cellulosic fiber is dipped or immersed into the mixture containing the POM or metal compound for several hours to days at a temperature of from 0° C. to 100° C., preferably for 2 hours to 2 days at from 25° C. to 80° C. In another embodiment, the POM or metal compound can be admixed with a resin or adhesive, and the resultant adhesive is applied to the surface of or admixed with the fabric or cellulosic fiber.

Typically, once the material has been contacted with the POM or metal compound mixture, the polyoxometalate material or non-POM material is dried in order to remove residual solvent. In one embodiment, the polyoxometalate materials or non-POM material is heated from 0° C. to 220° C. at or below atmospheric pressure, preferably from 25° C. to 100° C. In another embodiment, the polyoxometalate material or non-POM material is dried in vacuo (i.e., less than or equal to 10 torr).

In another embodiment, when the material is a fabric or cellulosic figber, the POM or metal compound can be incorporated into the fabric or cellulosic fiber by depositing the POM or metal compound on the surface of an existing fabric or cellulosic fiber, covalently bonding the POM or metal compound to the fibers of the fabric or cellulosic fiber, impregnating or intimately mixing the POM or metal compound with the fabric or cellulosic fiber, electrostatically bonding the POM or metal compound to the fabric or cellulosic fiber, or datively bonding the POM or metal compound to the fabric or cellulosic fiber via the coordination of a d- or f-block metal ion on the surface of the POM or metal compound with a functional group on the fabric. In the case of electrostatically bonding the POM to the fabric or cellulosic fiber, the positively charged functional groups on the fabric or cellulosic fiber and the negatively charged POM can form an electrostatic bond. In one embodiment, when the counterion of the polyoxometalate is a proton or the metal compound is an acid, the fabric or cellulosic fiber can be protonated by the polyoxometalate or metal compound to produce a positively charged fiber, which then electrostatically bonds to the polyoxometalate or metal compound anion. In one embodiment, a cationic polymer can be used as a binding agent to incorporate an anionic polyoxometalate or metal compound into an anionic fiber.

EXAMPLES

The following examples are put forth so as to provide those of ordinary skill in the art with a complete disclosure and description of how the compositions, materials, and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, target odorants/toxics are expressed in parts per million, temperature is in ° C. or is at ambient temperature and pressure is at or near atmospheric.

The term "consumption" or "consumed" refers to the removal or adsorption of a contaminant or contaminants from the environment or the conversion of the contaminant or contaminants to another compound that is nontoxic and/or non-malodorous.

General Considerations

Materials. PFPE #1511 is composed of 35–50% polytetrafluoroethylene thickening agent dispersed in a perfluoropolyether oil with water as a co-surfactant. PFPE #1511 was provided by Dr. E. H. Braue of the United States Army Medical Research Institute for Chemical Defense.

All reagents used in the examples were obtained from Aldrich Chemical Company, Milwaukee, Wis., and were used without further purification. The following reagents were used in the examples (the purity of the reagent is in parenthesis): CEES (98%), HPLC grade acetonitrile, tetrafluoroethylene (99.5%), 1,3-dichlorobenzene (98%), dimethyl sulfoxide (DMSO) (99.8%), $AgNO_3$ (99+%), $HAuCl_4$ (99+%), $CuCl_2$ (99+%), $FeCl_3$ (98%), $AgClO_4$ (99.9%), $(NEt_4)AuCl_2$, $CuSO_4$ (99.99%), $MnSO_4$ (98%), $VOSO_4$ (99.99%), $Ti(SO_4)_2$ (99%), $Fe_2(SO_4)_3$ (97%), $NiSO_4$ (99%), $ZnSO_4$ (99.99%), $Cr_2(SO_4)_3$ (99.999%), $MgSO_4$ (99%), $CoSO_4$ (99.998%), $Pd(NO_3)_4$ (98%), $Na_2SO_3$ (99%), and $NBu_4NO_3$ (97%). $NBu_4NO_2$ (98%) was purchased from Fluka.

Synthesis of $Ag_xNa_{5-x}PV_2Mo_{10}O_{40}$ $Na_5PV_2Mo_{10}O_{40}$ was prepared by the literature procedure outlined in Petterson, L.; Anderson, I.; Selling, A.; Grate, J. H. *Inorg. Chem.* 1994, 33, 982. $Ag_xNa_{5-x}PV_2Mo_{10}O_{40}$ was prepared using the following procedure. Ground $H_5PV_2Mo_{10}O_{40}$ (30.9 g, $1.78 \times 10^{-2}$ mol) was dissolved in 200 mL of distilled water. The orange solution was filtered three times to remove any undissolved POM. Ground $AgNO_3$ (15.2 g, $8.94 \times 10^{-2}$ mol) was added with vigorous stirring. The mixture was stirred overnight at room temperature. The product precipitated as a dark red-orange powder and was removed by suction filtration over a medium fritted glass funnel. The product was dried in vacuo overnight. The IR spectrum of the resultant powder confirmed the formation of $Ag_xNa_{5-x}PV_2Mo_{10}O_{40}$.

Synthesis of Additional Polyoxmetalates

The following POMs listed in Table 8 were prepared by literature procedures (the entry number in Table 8 and the bibliographical information are in parenthesis):

$Na_5CUPW_{11}O_{39}$; $Na_5MnPW_{11}O_{39}$; $K_5MnPW_{11}O_{39}$; and $K_5CoPW_{11}O_{39}$: (Entries 2–4 and, 6, respectively; Maksimov, G. M.; Kustova, G. N.; Matveev, K. I.; Lazarenko, T. P *Koord. Khim.* 1989, 15(6), 788–96).

$Na_5PV_2Mo_{10}O_{40}$ and $H_5PV_2Mo_{10}O_{40}$: (Entries 7 and 20, respectively; O'Donnell, Stephen E.; Pope, Michael T. *J. Chem. Soc., Dalton Trans.* 1976, 21, 2290–7).

$Na_4PVMo_{11}O_{40}$: (Entry 11; So, Hyunsoo; Pope, Michael T. *Inorg. Chem.* 1972, 11(6), 1441–3).

$Na_6PV_3Mo_9O_{40}$ and $H_6PV_3Mo_9O_{40}$: (Entries 8 and 21, respectively; Pope, Michael T.; O'Donnell, Stephen E.; Prados, Ronald A. *J. Chem. Soc., Chem. Commun.* 1975, 1, 22–3).

$Na_5H_2PV_4Mo_8O_{40}$ and $H_7PV_4Mo_8O_{40}$: (Entries 9 and 22, respectively; Yurchei E. N. *J. Mol. Struct.* 1980, 60, 325–31).

$Na_5FeSiW_{11}O_{39}$ and $K_6FeSiW_{11}O_{39}$: (Entries 12 and 36, respectively; Peacock, R. D.; Weakley, T. J. R. *J. Chem. Soc. A* 1971, 12, 1937–400).

$Na_5SiVW_{11}O_{40}$: (Entry 13; Tourne, Claude; Tourne, Gilbert. *Bull. Soc. Chim. Fr.* 1969, 4, 1124–36).

$K_8Co(II)P_2W_{17}O_{61}$: (Entry 15; Marcu, Gheorghe; Patrut, Adrian; Botar, Alexandru. *Rev. Chim. (Bucharest)* 1989, 40(11), 870–5).

$K_{12}Pd_3(PW_9O_{34})_2$: (Entry 16; Kuznietsova, N. I.; Kuznetsova, L. I.; Detusheva, L. G.; Likholobov, V. A.; Fedotov, M. A.; Koscheev, S. V.; Burgina, E. B. *Stud. Surf. Sci. Catal.* 1997, 110 (3rd World Congress on Oxidation Catalysis, 1997), 1203–1211).

$K_8Cu(II)P_2W_{17}O_{61}$: (Entry 17; Hamlaoui, Mohamed Larbi; Vlassenko, Konstantin; Messadi, Djelloul. C. R. *l'Academie Sci., Ser. II Univers* 1990, 311(7), 795–8).

$Na_4PVMo_{11}O_{40}$ and $Na_3PMo_{12}O_{40}$: (Entries 18 and 19, respectively; So, Hyunsoo; Pope, Michael T. *Inorg. Chem.* 1972, 11(6), 1441–3).

$Na_{16}P_4W_{30}Cu_4O_{112}$: (Entry 24; Huang, Ru-Dan; Bei, Bao-Li; Wang, En-Bo; Li, Bai-Tao; Zhang, Su-Xia. *Gaodeng Xuexiao Huaxue Xuebao* 1998, 19(11), 1721–1723).

$K_{10}Ce(PW_{11}O_{39})_2$: (Entry 26; Peacock, R. D.; Weakley, T. J. R. *J. Chem. Soc. A* 1971, 12, 1937–40)

$K_7CuSiW_{11}O_{39}$ and $Na_7CuSiW_{11}O_{39}$: (Entries 27 and 30, respectively; Teze, Andre; Souchay, Pierre. C. R. *Acad. Sci., Ser. C* 1973, 276(19), 1525–8).

$Na_5NiPW_{11}O_{39}$: (Entry 31; Maksimov, G. M.; Kustova, G. N.; Matveev, K. I.; Lazarenko, T. P. *Koord. Khim.* 1989, 15(6), 788–96).

$Na_3AsW_{12}O_{40}$: (Entry 35; Tsyganok, L. P.; Statsenko, V. P.; Vil'dt, A. L. *Zh. Neorg. Khim.* 1974, 19(11), 3071–7).

$K_8NiP_2W_{17}O_{61}$: (Entry 37; Hamlaoui, Mohamed Larbi; Vlassenko, Konstantim; Messadi, Djelloul. C. R. *l'Academe Sci., Ser. II Univers* 1990, 311(7), 795–8).

$(Me_4N)_{10}(Co_3SiW_9O_{40}H_6)$: (Entry 38; Nomiya, Kenji; Miwa, Makoto. *Polyhedron* 1985, 4(8), 1407–12).

$Na_3V_{10}O_{28}$: (Entry 40; Preuss, F.; Rosenhahn, L. *J. Inorg. Nucl. Chem.* 1972, 34(5), 1691–703).

$K_8P_2W_{17}(NbO_2)O_{61}$: (Entry 42; Gong, Jian; Li, Guoping; Wang, Fuquan; Qu, Lunyu. *Wuji Huaxue Xuebao* 1995, 11(3), 232–7).

$(NH_4)_6P_2FeW_{17}O_{61}$,: (Entry 43; Peacock, R. D.; Weakley, T. J. R. *J. Chem. Soc. A* 1971, Issue 12, 1937–40).

$K_7Mn(II)P_2W_{17}O_{61}$: (Entry 44; Marcu, Gheorghe; Patrut, Adrian; Botar, Alexaudru. (1). *Rev. Chim. (Bucharest)* 1989, 40(11), 870–5).

$(NH_4)_6P_2W_{18}O_{62}$: (Entry 50; Varga, Gideon M., Jr.; Papaconstanitinou, Elias; Pope, Michael T. *Inorg. Chem.* 1970, 9(3), 662–7).

$Na_9PV_6Mo_6O_{40}$: (Entry 1; Ret'yakov, V. P.; Volkova, L. K.; Zimtseva, G. P.; Rudakov, E. S. *Kinet. Katal.* 1993, 34(1), 183).

$K_{12}Cu_3(W_9PO_{34})_2$: (Entry 10; Weakly, Timothy J. R.; Finke, Richard G. *Inorg. Chem.* 1990, 29(6), 1235–41).

$K(NH_4)_6RuBW_{11}O_{39}$: (Entry 34; Liu, Huizlhaiig; Sun, Wenliang; Yue, Bun; Li, Mingxing; Chen, Zhijiang; Jin, Songlin; Xie, Gaoyang; Shao, Qianfen; Wu, Tailiu; Chen, Shiming; Yan, Xiaoming. *Wuji Huaxue Xuebao* 1997, 13(3), 251–257).

$K_{10}Ni_4P_2W_{17}O_{61}$: (Entry 14; Yon, David K.; Miller, Warren K.; Novet, Thomas; Domaille, Peter J.; Evitt, Eric; Johnson, David C.; Finke, Richard G. *J. Am. Chem. Soc.* 1991,113(19), 7209–21).

$K_{10}Co_4P_2W_{18}O_{68}$: (Entry 39; Evans, Howard T.; Tourne, Claude M.; Toume, Gilbert F.; Weakley, Timothy J. R. *J. Chem. Soc., Dalton Trans.* 1986, 12, 2699–705).

$K_{10}Mn4(PW_9O_{34})_2$: (Entry 41; Gomez-Garcia, C. J.; Coronado, E.; Gomez-Romero, P.; Casan-Pastor, N. *Inorg. Chem.* 1993, 32(15), 3378–81).

$K_{10}Cu_4P_2W_{18}O_{68}$: (Entry 45; Weakley, Timothy J. R.; Finke, Richard G. *Inorg. Chem.* 1991, 29(6), 1235–41).

$K_{12}P_2W_{18}Ni_3O_{68}$: (Entry 47; Gomez-Garcia, Carlos J.; Coronado, Eugenio; Ouahab, Lahcene. *Angew. Chem.* 1992, 104(5), 660–2).

$Na_6P_4W_{30}Mn(II)_4O_{112}$: (Entry 49; Gomez-Garcia, C. J.; Borras-Almenar, J. J.; Coronado, E.; Ouahab, L. *Inorg. Chem.* 1994, 33(18), 4016–22).

$K_8Co_2W_{11}O_{39}$: (Entry 29; Walmsley, F. *J. Chem Ed.* 1992, 69(11), 936–38).

$(NH_4)_{17}Na(NaSb_9W_{21})O_{86}$: (Entry 51; Minami, N.; Hiraoka, M.; Izumni, K.; Uchida, Y. Japanese Patent JP 08113731 A2 1996, *Chem. Abstr.* 1996, 125, 117542).

$Na_3H_3PMo_9O_{34}$: (Entry 48; Inouye, Y.; Tokutake, Y.; Kunihara, J.; Yoshida, T.; Yamase, Y.; Nakata, A.; Nakamura, S. *Chem. Pharm. Bull.* 1992, 40, 805–807).

$K_8COVW_{11}O_{40}$: (Entry 28; Bas-Serra, J.; Todorut, et al. *Synth. React. Inorg. Met.-Org. Chem.* 1995, 25(6), 869–82).

$H_2Na_{14}[Fe(III)_2(Na_2O)_2(P_2W_{15}O_{56})_2]$: (Entry 25; Shigeta, S.; Mori, S.; Watanbe, J.; Baba, M.; Khenkin, A. M.; Hill, C. L.; Schinazi, R. F. *Antiviral Chem. Chemother.* 1996, 346–352).

$K_6SiTiW_{11}O_{40}$: (Entry 33; Blasecki, J. W. *Top. Mol. Org. Eng.* 1994, 10, 373–385).

$K_8Cu(II)P_2W_{17}O_{61}$: (Entry 17; Marc, Gheorghe; Patrut, Adrian; Botar, Alexandru. *Rev. Chim. (Bucharest)* 1989, 40(11), 870–5).

$(n\text{-}Dec_4)_6HMnNb_3P_2W_{15}O_{62}$: (Entry 5; Gong, J., Chen, et al. *Polyhedron*, 1996, 15, 2273–7).

The following POMs were prepared by the following experimental procedures.

$K_5Si(NbO_2)W_{11}O_{40}$ (Entry 46): 1.0 g of $K_7HNb_6O_{16}$ was dissolved in 75-mL of deionized $H_2O$. To this solution, 2-mL of 30% $H_2O_2$ was added. A few drops of 3M HCl were to bring the pH to approximately 6. $K_8SiW_{11}O_{39}$ (15.8 g) was added, which resulted in gas evolution. To the swirling mixture, 25-mL of $H_2O$ followed by 12-mL of 3M HCl were added. The color of the solution was yellow and the pH was approximately 1. The mixture was stirred for an additional 30 minutes, then 14 g of solid KCl was added, which resulted in the information of a pale yellow solid. The solid was collected by filtration and resulting in 4.7 g of $K_5Si(NbO_2)W_{11}O_{40}$.

$Na_6SiVNbW_{11}O_{39}$ (Entry 32): 6.64 g of $K_7Hb_6O_{19}$ was dissolved in 800-mL of $H_2O$. To this solution, 80-mL of 30% $H_2O$ solution was added and the pH was adjusted to 6.0 with KOH. Solid $K_9SiVW_{10}O_{39}$ was added slowly to produce a final pH of 8.5. To this mixture, 40-mL of 3M HCl was added dropwise. The addition was stopped occasionally to agitate the solid. The solution was then stirred for 15 minutes. Additional 3M HCl (40-mL) was added to give a pH of 1.5. The solution was stirred for 1 hour, and 160 g of solid KCl was added. The orange precipitate was filtered off and dried, yielding 40.85 g of $K_6SiVNbW_{11}O_{39}$. $K_6SiVNbW_{11}O_{39}$ and water were pass through as Amberlite IR-120 ion exchange column which was charged with 1 M NaCl. The volatiles were removed from the collected solution by vacuum to produce $Na_6SiVNbW_{11}O_{39}$ as a yellow, crystalline solid. The amberlite is a product of Rohm and Haas and was purchased from Aldrich.

Instrumentation. Gas chromatography analysis was conducted using a Hewlett-Packard Series 5890 Gas Chromatograph equipped with a flame ionization detector and fitted with non-polar 5% PHME siloxane, 30 meter column. Alternatively, the gas chromatograph was equipped with all FID detector and a 5% phenyl methyl silicone capillary column. Mass abundance determinations were performed using a HP 5890 GC with a 5% phenyl methyl silicone capillary column and a 5971A Mass Selective Detector. Gas chromatography/mass spectroscopy was performed using a Hewlett-Packard Series II 5890 Gas Chromatograph equipped with a 5971A mass selective detector and fitted with a non-polar 5% PHME siloxane, 25 meter column. For both GC and GC-MS, nitrogen was used as the carrier gas. In Examples 5 and 6, all reactions were monitored using a Hewlett-Packard 6890 gas chromatograph with flame ionization and HP-5 (5% phenylmethylsilicone capillary column. UV-visible spectra were run on a HP 8452A Diode Array Spectrophotometer. The percentages of $O_2$ of the reaction atmosphere were varied using a Series 810 Mass Trak flowmeter with dried argon as the other gas.

Example 1
Oxidation of CEES to CEESO by a POM/TSP Mixture Under Ambient Conditions after 40 Days PFPE #1511 (0.525 g) was combined with $Ag_xNa_{5-x}PV_2Mo_{10}O_{40}$ (0.066 g, $3.81 \times 10^{-5}$ mol) to give a 11% weight/weight POM/cream mixture. The POM/cream mixture was placed in a 18 mL glass vial fitted with a poly (tetrafluoroethylene) (PTFE) stopper. A sufficient amount of 2-chloroethyl ethyl sulfide (CEES) was added to the mixture to completely submerge the POM/cream mixture. After 40 days, 10 μL of the CEES solution surrounding the POM/cream mixture was removed and diluted into 100 μL of 2,2,2-trifluoroethanol (TFE). GC-MS of this solution showed the presence of 2-chloroethyl ethyl suboxide (CEESO).

Example 2
Oxidation of CEES to CEESO by POM/TSP Mixtures Under Ambient Conditions The CEES composition used in all trials was composed of 9.0 mL of CEES combined with 100 μL of 1,3-dichlorobenzene, where the 1,3-dichlorobenzene was added as an internal reference. Each POM/PFPE #1511 cream mixture (approximately 0.3 g) was smeared at the bottom of an 18 mL glass vial and fitted with a PTFE cap. The CEES composition (1.0 mL) was then added and each vial was left undisturbed for several days under ambient conditions, with periodic GC analysis of the CEES/reference solution to check for CEESO formation. For GC analysis, 10 μL of the CEES/reference solution surrounding the POM/cream mixture was diluted in 100 μL of TFE and analyzed. The results are shown in Table 1.

TABLE 1

| Entry | Catalyst | Weight Percent[a] | Turnovers after 9 Days[b] |
|---|---|---|---|
| 1 | cream only | N/A | 0 |
| 2 | $AgNO_3$ | 20.3% | 0 |
| 3 | $H_5PV_2Mo_{10}O_{40}$ | 5.8% | 0 |
| 4 | $H_5PV_2Mo_{10}O_{40}$ | 20.8% | 0 |
| 5 | $Ag_xNa_{5-x}PV_2Mo_{10}O_{40}$ | 5.6% | 0 |
| 6 | $Ag_xNa_{5-x}PV_2Mo_{10}O_{40}$ | 20.6% | 0 |
| 7 | $HAuCl_4$ | 7.1% | 0 |
| 8 | $HAuCl_4$, $AgNO_3$ $AgClO_4$[c] | 7.6% | 5 |

[a]Weight Percent = (mass of POM (g))/(mass of cream (g) + mass of POM (g)) × 100
[b]Turnovers = (mol of CEESO/mol of catalyst) × 100
[c]This mixture was composed of 1 equiv. of $HAuCl_4$, 1.25 equiv. of $AgClO_4$, and 0.75 equiv. of $AgNO_3$. The weight percent is reported as the (weight of all components, g)/(weight of cream, g + weight of components, g) × 100

Example 3
Catalytic Oxidation of CEES by POMs in 2,2,2-Trifluoroethanol After 14 Days Under Ambient Conditions A CEES solution was prepared by mixing 85.8 mM of CEES; $1.51 \times 10^{-5}$ to $1.82 \times 10^{-5}$ mol of catalyst; 100 μL 1,3-dichlorobenzene (internal standard); and 85 mL of 2,2,2-trifluoroethanol, at 25° C. under ambient air. In a typical run, 5.0 mL of the CEES solution was combined with enough catalyst to yield a CEES:POM ratio of 20:1, and the mixture was stirred for 14 days. The results are shown in Table 2.

TABLE 2

| Entry | Catalyst | CEESO Turnovers[a] |
|---|---|---|
| 1 | $AgNO_3$ | 0.42 |
| 2 | $Ag_xH_{5-x}PV_2Mo_{10}O_{40}$ | 8.13 |
| 3 | $Ag_xH_{4-x}PVMo_{11}O_{40}$ | 1.18 |
| 4 | $Na_5PV_2MO_{10}O_{40}$ | 0.00 |
| 5 | $K_5CoVW_{11}O_{40}$ | 0.00 |
| 6 | $K_5Cu^{II}PW_{11}O_{39}$ | 15.33 |
| 7 | $Ag_xK_{12-x}Ce(PW_{11}O_{39})_2$ | 4.47 |
| 8 | $(NH_4)_2Ce(NO_3)_6$ | 18.53 |
| 9 | $Ag_xK_{5-x}Cu^{II}PW_{11}O_{39}$ | 15.21 |

[a]Turnovers = (mol of CEESO/mol of catalyst) × 100

Example 4
Aerobic Oxidation of Acetaldehyde Catalyzed by Polyoxometalates

In a 20 mL vial, 0.961 mmol acetaldehyde, 2 mg of POM, and pentane (internal standard) (34.7 μL) were stirred in 2 mL of chlorobenzene under 20 mL (0.82 mmol) of $O_2$ at 298 K for 24 hours. Under these conditions, the POM was totally insoluble at all times during the reaction. For the cloth samples, the polyoxometalate was deposited as a 5% by weight solution of $H_2O$ and subsequently dried. BHT (2,6-di-tert-butyl-p-cresol) was used as a radical inhibitor in a 1.2 mol ratio versus POM. The aerobic oxidation of acetaldehyde by the POMs is shown in Table 3.

TABLE 3

| Entry | Catalyst | Time (h) | Equivalents $CH_3CHO^a$ | % Conversion of Acetaldehyde[b] | % Yield Acetic Acid[c] | Turnovers[d] |
|---|---|---|---|---|---|---|
| 1 | Blank | 24 | — | 8 | 0 | — |
| 2 | $Na_8Co_2W_{11}O_{39}$ | 24 | 1538 | 97.8 | 67.2 | 1033 |
| 3 | $K_8SiCoVW_{10}O_{39}$ | 24 | 1521 | 95.7 | 60.2 | 916 |
| 4 | $K_7SiCoVW_{10}O_{39}$ | 24 | 1483 | 92.3 | 55.8 | 827 |
| 5 | Blank | 28.5 | — | 37 | 10 | — |
| 6 | $Na_8Co_2W_{11}O_{39}$ | 28.5 | 3075 | 80.3 | 70.3 | 1844 |
| 7 | $K_8SiCoVW_{10}O_{39}$ | 28.5 | 3041 | 72.1 | 59.4 | 1491 |
| 7 | $K_7SiCoVW_{10}O_{39}$ | 28.5 | 2966 | 73.3 | 62.4 | 1545 |
| 8 | Cotton-$Na_8Co_2W_{11}O_{39}$ | 24 | 1538 | 98.2 | 66.2 | 815 |
| 9 | Cotton-$K_8SiCoVW_{10}O_{39}$ | 24 | 1521 | 90.4 | 50.0 | 644 |
| 10 | 1 $Na_8Co_2W_{11}O_{39}$/ 1.2 BHT | 24 | 1538 | 17.8 | 22.4 | 180 |

[a]Equivalents of Acetaldehyde = moles of acetaldehyde (material)/moles of POM. For the last three reactions (Entries 5–8) after 24 h another 0.961 mmol acetaldehyde was added, and the suspension was allowed to stir for an additional 8 h. All values are averages of two experiments.
[b]% Conversion = (moles of acetaldehyde consumed/moles of initial acetaldehyde) × 100.
[c]% Yield = (moles of acetic acid/moles of initial acetaldehyde) × 100.
[d]Turnovers = [moles of acetic acid (in the run with catalyst) − moles of acetic acid (in the blank run without catalyst)]/moles of catalyst.

Example 5

Aerobic Oxidation of Tetrahydrothiophene in Liquid Phase by Modified Polyoxometalates and Metal Compounds Tetrahydrothiophene (THT) (0.445 mmol, 0.64 M) and 1,3-dichlorobenzene (internal standard) in the presence or absence of the polyoxometalates and/or metal compound were stirred in 4 mL of acetonitrile in 20 mL vials under 1 atm $O_2$ at room temperature. The aerobic oxidation of THT by modified polyoxometalates and metal compound is shown in Table 4. In Entries 3–7 and 12, $2 \times 10^{-6}$ mol of polyoxometalate or metal compound was placed in the before adding the reagent and internal standard. In Entries 8–14, polyoxometalates and metal compound (Entries 11 and 14) or the metal compounds were placed in the vial before the addition of the reagent and the internal standard. In Entries 8–14, $2 \times 10^{-6}$ mol of each POM or metal compound was used in a 1/1 ratio.

TABLE 4

| Entry | Catalyst | Time (h) | Yield %[a] | Turnover[b] |
|---|---|---|---|---|
| 1 | Blank[c] | 3.5 | 0 | — |
| 2 | Blank[c] | 72[d] | 0 | — |
| 3 | $H_5PV_2Mo_{10}O_{40}$ | 3.5 | 0 | 0 |
| 4 | $HAuCl_4$ | 3.5 | 0 | 0 |
| 5 | $HAuCl_4$ | 72[d] | 0 | 0 |
| 6 | $(NH_4)_2Ce(NO_3)_6$ | 3.5 | 14 | 12 |
| 7 | $(NH_4)_2Ce(NO_3)_6$ | 72[d] | 26 | 100 |
| 8 | $(NH_4)_2Ce(NO_3)_6 + H_5PV_2Mo_{10}O_{40}$ | 3.5 | 14 | 12 |
| 9 | $(NH_4)_2Ce(NO_3)_6 + HAuCl_4$ | 3.5 | 67 | 57 |
| 10 | $(NH_4)_2Ce(NO_3)_6 + HAuCl_4$ | 72[d] | 76 | 293 |
| 11 | $(NH_4)_2Ce(NO_3)_6 + HAuCl_4 + H_5PV_2Mo_{10}O_{40}$ | 3.5 | 65 | 56 |
| 12 | $H_2PtCl_6$ | 3 | 0 | 0 |
| 13 | $(NH_4)_2Ce(NO_3)_6 + H_2PtCl_6$ | 3 | 25 | 21 |
| 14 | $(NH_4)_2Ce(NO_3)_6 + H_2PtCl_6 + H_5PV_2Mo_{10}O_{40}$ | 3 | 26 | 23 |

[a]Moles of THTO/moles of initial THT.
[b]Moles of THTO/moles of catalyst.
[c]No catalysts.
[d]More THT and $O_2$ added to the reaction system after 24 hr of initial reaction.

Example 6

Aerobic Oxidation of CEES in Liquid Phase by Modified Polyoxometalates and Metal Compounds CEES (0.337 mmol, 0.64 M) and 1,3-dichlorobenzene (internal standard) in the presence or absence of the polyoxometalates and/or metal compound were stirred in 4 mL of acetonitrile in 20 mL vials under 1 atm of $O_2$ at room temperature. The aerobic oxidation of CEES by modified polyoxometalates and metal compounds is shown in Table 5. In Entries 2, 3, 5, and 6, $2 \times 10^{-6}$ mol of polyoxometalates or metal compound was placed in vial before adding the reagent. In Entries 4 and 7–12, the polyoxometalates and/or the metal compound(s) ($2 \times 10^{-6}$ mol) were placed in vial before adding the reagent solution.

TABLE 5

| Entry | Catalyst | Time (day) | Conversion %[a] | Yield %[b] | Turnover[c] |
|---|---|---|---|---|---|
| 1 | Blank[d] | 3 | 0 | 0 | — |
| 2 | $HAuCl_4$ | 3 | 0 | 0 | 0 |
| 3 | $H_5PV_2Mo_{10}O_{40}$ | 3 | 1 | 0 | 0 |
| 4 | $HAuCl_4 + H_5PV_2Mo_{10}O_{40}$ | 3 | 12 | 3 | 2 |
| 5 | $(NH_4)_2Ce(NO_3)_6$ | 1 | 16 | 8 | 5 |
| 6 | $(NH_4)_2Ce(NO_3)_6$ | 3 | 26 | 18 | 12 |
| 7 | $(NH_4)_2Ce(NO_3)_6 + HAuCl_4$ | 1 | 28 | 9 | 6 |
| 8 | $(NH_4)_2Ce(NO_3)_6 + HAuCl_4$ | 3 | 57 | 36 | 24 |
| 9 | $(NH_4)_2Ce(NO_3)_6 + H_5PV_2Mo_{10}O_{40}$ | 1 | 47 | 24 | 15 |
| 10 | $(NH_4)_2Ce(NO_3)_6 + H_5PV_2Mo_{10}O_{40}$ | 3 | 64 | 41 | 27 |
| 11 | $(NH_4)_2Ce(NO_3)_6 + HAuCl_4 + H_5PV_2Mo_{10}O_{40}$ | 1 | 53 | 43 | 28 |
| 12 | $(NH_4)_2Ce(NO_3)_6 + HAuCl_4 + H_5PV_2Mo_{10}O_{40}$ | 3 | 82 | 70 | 46 |

[a]Moles of CEES consumed/moles of initial CEES.
[b]Moles of CEESO (the GC response factor of CEESO is assumed the same as that of CEES)/moles of initial CEES.
[c]Moles of CEESO (the GC response factor of CEESO is assumed the same as that of CEES)/moles of catalyst.
[d]No catalyst.

Example 7

Aerobic Oxidation of CEES in Liquid Phase by a Polyoxometalates and $HAuCl_4$

Each POM ($9.61 \times 10^{-6}$ mol); $HAuCl_4$ ($4.8 \times 10^{-5}$ mol); 1,3-dichlorobenzene ($9.61 \times 10^{-4}$ mol), and CEES ($9.61 \times 10^{-4}$ mol) were stirred in 4 mL acetonitrile under 20 mL (0.82 mmol) of $O_2$ at 298 K. The aerobic oxidation is shown in Table 6.

TABLE 6

| Entry | Catalyst | Time (h) | Turnovers[a] of CEESO | Time (h) | Turnovers[b] of CEESO |
|---|---|---|---|---|---|
| 1 | $Na_4PVMo_{11}O_{40}$ | 4 | 0 | 11 | 1.1 |
| 2 | $Na_5PV_2Mo_{10}O_{40}$ | 4 | 5.0 | 11 | 10.6 |

TABLE 6-continued

| Entry | Catalyst | Time (h) | Turnovers[a] of CEESO | Time (h) | Turnovers[b] of CEESO |
|---|---|---|---|---|---|
| 3 | $Na_6PV_3Mo_9O_{40}$ | 4 | 7.0 | 11 | 18.3 |
| 4 | $Na_5H_2PV_4W_8O_{40}$ | 4 | 4.4 | 11 | 14.2 |
| 5 | $Na_9PV_6Mo_6O_{40}$ | 4 | 5.6 | 11 | 20.7 |
| 6 | $Na_5CuPW_{11}O_{39}$ | 4 | 59.2 | 11 | 83.6 |
| 7 | $HAuCl_4$ | 4 | 0 | 11 | 0 |

[a]Turnovers = (moles of CEESO (catalyst run) − moles of CEESO (blank run))/moles of catalyst.

Example 8
Aerobic Catalytic Oxidation of CEES to the Sulfoxide (CEESO) Using $AgNO_3/HAuCl_4$ System (Non-POM system)

A metal compound solution was prepared by combining $AgNO_3$ ($1.0\times10^{-5}$ mol) and $HAuCl_4$ ($5.0\times10^{-6}$ mol) in 1 mL acetonitrile. To this solution was added CEES ($3.0\times10^{-3}$ mol). Upon addition of CEES to the solution, a white precipitate immediately formed. The precipitate is believed to be silver containing salt, possibly coordinated to CEES. The solution was allowed to stirred for 100 hours, at which time there was loss of CEES in the solution based on gas chromatography. The filtrate was taken to dryness, and a solution containing excess CEES in acetonitrile was added to the yellow oily residue. Gas chromatography of the solution confirmed the formation of CEESO. The results are shown in Table 7 (entries 1–7).

Example 9
Aerobic Catalyzed Oxidation of CEES to the Sulfoxide (CEESO) Using $AgNO_3/AgClO_4/HAuCl_4$ System (Non-POM system)

A 20 mL vial fitted with a PTFE septum was purged with 1 atm of $O_2$. To this vial were added by syringe, 0.035 mL of $AgNO_3$ (0.1013 M in acetonitrile); 0.060 mL of $AgClO_4$ (0.1138 M in acetonitrile); and 0.100 mL $HAuCl_4$ (0.0477 M in acetonitrile), and the total volume was adjusted to 1 mL with addition of HPLC grade acetonitrile. To this solution, 0.36 mL ($2.86\times10^{-3}$ mol) of CEES were added to the solution, and the formation of CEESO was monitored over time by gas chromatography using 1,3-dichlorobenzene as the internal reference. The results are summarized in Table 7 (Entries 8–11).

TABLE 7

| Entry | Catalyst | Time (hrs) | Turnover[a] |
|---|---|---|---|
| 1 | 2 $AgNO_3$ | 100 | 0 |
| 2 | 2 $AgClO_4$ | 100 | 0 |
| 3 | 1 $HAuCl_4$ | 100 | 0.9 |
| 4 | 2 $AgNO_3$ + 1 $HAuCl_4$ | 1 | 13.0 |
| 5 | 2 $AgNO_3$ + 1 $HAuCl_4$ | 2 | 21.3 |
| 6 | 2 $AgNO_3$ + 1 $HAuCl_4$ | 24 | 83.5 |
| 7 | 2 $AgNO_3$ + 1$HAuCl_4$ | 100 | 146.3 |
| 8 | 0.75$AgNO_3$ + 1.25$AgCl_4$ + 1$HAuCl_4$ | 1 | 38.3 |
| 9 | 0.75$AgNO_3$ + 1.25$AgCl_4$ + 1$HAuCl_4$ | 2 | 50.2 |
| 10 | 0.75$AgNO_3$ + 1.25$AgCl_4$ + 1$HAuCl_4$ | 24 | 141.9 |
| 11 | 0.75$AgNO_3$ + 1.25$AgCl_4$ + 1$HAuCl_4$ | 100 | 208.7 |

[a]Moles of CEESO/moles of catalyst (catalyst is based on moles of $HAuCl_4$ used).

Example 10
Aerobic Oxidation of CEES by POM/$HAuCl_4$ and Metal Compound/$HAuCl_4$ Systems One equivalent of the POM or metal compound was combined with five equivalents of $HAuCl_4$ in acetonitrile, wherein the total volume was 1 mL. To this solution, 100 equivalents of CEES was added. The reaction was conducted under one atm $O_2$ at 298 K. The number of turnovers were calculated at 4 and 11 hours, and the results are summarized in Table 8a TABLE 8a

| Entry | POM or Metal Compound | Turnovers[a] | Turn-overs[b] |
|---|---|---|---|
| 1 | $Na_9PV_6Mo_6O_{40}$ | 5.6 | 20.7 |
| 2 | $Na_5CuPW_{11}O_{39}$ | 59.2 | 83.6 |
| 3 | $Na_5MnPW_{11}O_{39}$ | 6.5 | 29.0 |
| 4 | $K_5CoPW_{11}O_{39}$ | 38.9 | 71.9 |
| 5 | $(n-Dec_4)_6HMnNb_3P_2W_{15}O_{62}$ | 5.1 | 27.9 |
| 6 | $K_5PMnW_{11}O_{39}$ | 51.8 | 76.5 |
| 7 | $Na_5PV_2Mo_{10}O_{40}$ | 5.0 | 10.6 |
| 8 | $Na_6PV_3Mo_9O_{40}$ | 7.0 | 18.3 |
| 9 | $Na_5H_2PV_4Mo_8O_{40}$ | 4.4 | 14.2 |
| 10 | $K_{12}Cu_3(W_9PO_{34})_2$ | 5.1 | 12.2 |
| 11 | $Na_4PVW_{11}O_{39}$ | 1.6 | 8.7 |
| 12 | $Na_5FeSiW_{11}O_{40}$ | 0.9 | 4.6 |
| 13 | $Na_5SiVW_{11}O_{40}$ | 0.0 | 2.3 |
| 14 | $K_{10}Ni_4P_2W_{17}O_{61}$ | 3.5 | 7.5 |
| 15 | $K_8Co(II)P_2W_{17}O_{61}$ | 1.0 | 2.5 |
| 16 | $K_{12}Pd_3(PW_9O_{34})_2$ | 4.2 | 6.4 |
| 17 | $K_8Cu(II)P_2W_{17}O_{61}$ | 2.0 | 4.7 |
| 18 | $Na_4PVMo_{11}O_{40}$ | 0.0 | 1.2 |
| 19 | $Na_3PMo_{12}O_{40}$ | 0.0 | 0.1 |
| 20 | $H_5PV_2W_{10}O_{40}$ | 0.0 | 1.4 |
| 21 | $H_6PV_3W_9O_{40}$ | 0.0 | 1.2 |
| 22 | $H_7PV_4W_8O_{40}$ | 0.0 | 0.9 |
| 23 | $HAuCl_4$ | 0.0 | 0.0 |
| 24 | $Na_{16}P_4W_{30}Cu_4O_{112}$ | 1.5 | 1.5 |
| 25 | $H_2Na_{14}[Fe(III)_2(NaH_2O)_2(P_2W_{15}O_{56})_2]$ | 1.0 | 1.6 |
| 26 | $K_{10}Ce(PW_{11}O_{39})_2$ | 0.6 | 0.7 |
| 27 | $K_7CuSiW_{11}O_{39}$ | 1.0 | 1.1 |
| 28 | $K_8CoVW_{11}O_{40}$ | 1.3 | 1.1 |
| 29 | $K_8Co_2W_{11}O_{39}$ | 1.5 | 1.0 |
| 30 | $Na_7CuSiW_{11}O_{39}$ | 1.1 | 1.1 |
| 31 | $Na_5NiPW_{11}O_{39}$ | 0.6 | 0.9 |
| 32 | $Na_6SiVNbW_{11}O_{39}$ | 0.7 | 0.6 |
| 33 | $K_6SiTiW_{11}O_{40}$ | 0.6 | 0.4 |
| 34 | $K(NH_4)_6RuBW_{11}O_{39}$ | 0.7 | 0.9 |
| 35 | $Na_3AsW_{12}O_{40}$ | 0.7 | 0.2 |
| 36 | $K_6FeSiW_{11}O_{39}$ | 0.9 | 0.7 |
| 37 | $K_8NiP_2W_{17}O_{61}$ | 0.9 | 0.9 |
| 38 | $(Me_4N)_{10}(Co_3SiW_9O_{40}H_6)$ | 1.8 | 1.9 |
| 39 | $K_{10}Co_4P_2W_{18}O_{68}$ | 1.3 | 1.6 |
| 40 | $Na_3V_{10}O_{28}$ | 1.8 | 1.7 |
| 41 | $K_{10}Mn_4(PW_9O_{34})_2$ | 1.3 | 1.4 |
| 42 | $K_8P_2W_{17}(NbO_2)$ | 1.1 | 0.9 |
| 43 | $(NH_4)_6P_2FeW_{17}O_{61}$ | 0.6 | 0.5 |
| 44 | $K_2Mn(II)P_2W_{17}O_{61}$ | 1.0 | 0.8 |
| 45 | $K_{10}P_2W_{18}Cu_4O_{68}$ | 1.2 | 1.9 |
| 46 | $K_5Si(NbO_2)W_{11}O_{40}$ | 0.9 | 0.7 |
| 47 | $K_{12}P_2W_{18}Ni_3O_{68}$ | 1.0 | 1.8 |
| 48 | $Na_3H_3Mo_9O_{34}$ | 0.8 | 0.9 |
| 49 | $Na_6P_4W_{30}Mn(II)_4O_{112}$ | 1.1 | 1.4 |
| 50 | $(NH_4)_6P_2W_{18}O_{62}$ | 0.0 | 0.3 |
| 51 | $(NH_4)_{17}Na(NaSb_9W_{21})O_{86}$ | 0.5 | 1.8 |
| 52 | $CuCl_2$ | 0.0 | 0.4 |
| 53 | $FeCl_3$ | 0.3 | 0.5 |

[a]Turnovers after 4 hours
[b]Turnovers after 11 hours

TABLE 8b

| Entry | Compound A | Compound B |
|---|---|---|
| 1 | | 5 $HAuCl_4$ |
| 2 | $Na_4PVMo_{11}O_{40}$ | |
| 3 | $Na_4PVMo_{11}O_{40}$ | 5 $HAuCl_4$ |
| 4 | $Na_5PV_2Mo_{10}O_{40}$ | |
| 5 | $Na_5PV_2Mo_{10}O_{40}$ | 5 $HAuCl_4$ |
| 6 | $Na_6PV_3Mo_9O_{40}$ | |
| 7 | $Na_6PV_3Mo_9O_{40}$ | 5 $HAuCl_4$ |

TABLE 8b-continued

| Entry | Compound A | Compound B |
|---|---|---|
| 8 | $Na_5H_2PV_4Mo_8O_{40}$ | |
| 9 | $Na_5H_2PV_4Mo_8O_{40}$ | 5 $HAuCl_4$ |
| 10 | $Na_9PV_6Mo_6O_{40}$ | |
| 11 | $Na_9PV_6Mo_6O_{40}$ | 5 $HAuCl_4$ |
| 12 | $Na_4PVW_{11}O_{40}$ | |
| 13 | $Na_4PVW_{11}O_{40}$ | 5 $HAuCl_4$ |
| 14 | $Na_3PMo_{12}O_{40}$ | |
| 15 | $Na_3PMo_{12}O_{40}$ | 5 $HAuCl_4$ |
| 16 | $Na_5CuPW_{11}O_{39}$ | 5 $HAuCl_4$ |
| 17 | $(TBA)_5CuPW_{11}O_{39}$ | 5 $HAuCl_4$ |
| 18 | $Na_5MnPW_{11}O_{39}$ | |
| 19 | $Na_5MnPW_{11}O_{39}$ | 5 $HAuCl_4$ |
| 20 | $Na_5FeSiW_{11}O_{39}$ | |
| 21 | $Na_5FeSiW_{11}O_{39}$ | |
| 22 | $Na_5SiVW_{11}O_{40}$ | |
| 23 | $Na_5SiVW_{11}O_{40}$ | 5 $HAuCl_4$ |
| 24 | $Na_5PV_2W_{10}O_{40}$ | |
| 25 | $Na_5PV_2W_{10}O_{40}$ | 5 $HAuCl_4$ |
| 26 | $Na_6PV_3W_9O_{40}$ | |
| 27 | $Na_6PV_3W_9O_{40}$ | 5 $HAuCl_4$ |
| 28 | $Na_7PV_4W_8O_{40}$ | |
| 29 | $Na_7PV_4W_8O_{40}$ | 5 $HAuCl_4$ |
| 30 | $Na_{16}P_4W_{30}Cu_4O_{112}$ | |
| 31 | $Na_{16}P_4W_{30}Cu_4O_{112}$ | 5 $HAuCl_4$ |
| 32 | $H_2Na_{14}[Fe(III)_2(NaH_2O)_2(P_2W_{15}O_{56})_2$ | |
| 33 | $H_2Na_{14}[Fe(III)_2(NaH_2O)_2(P_2W_{15}O_{56})_2$ | 5 $HAuCl_4$ |
| 34 | $K_{10}Ce(PW_{11}O_{39})_2$ | |
| 35 | $K_{10}Ce(PW_{11}O_{39})_2$ | 5 $HAuCl_4$ |
| 36 | $K_7CuSiW_{11}O_{39}$ | |
| 37 | $K_7CuSiW_{11}O_{39}$ | 5 $HAuCl_4$ |
| 38 | $K_8CoVW_{11}O_{39}$ | |
| 39 | $K_8CoVW_{11}O_{39}$ | 5 $HAuCl_4$ |
| 40 | $K_5CoPW_{11}O_{39}$ | |
| 41 | $K_5CoPW_{11}O_{39}$ | 5 $HAuCl_4$ |
| 42 | $K_8Co_2W_{11}O_{39}$ | |
| 43 | $K_8Co_2W_{11}O_{39}$ | 5 $HAuCl_4$ |
| 44 | $(NDec_4)_6HMnNb_3P_2W_{15}O_{62}$ | |
| 45 | $(NDec_4)_6HMnNb_3P_2W_{15}O_{62}$ | 5 $HAuCl_4$ |
| 46 | $Na_7CuSiW_{11}O_{39}$ | |
| 47 | $Na_7CuSiW_{11}O_{39}$ | 5 $HAuCl_4$ |
| 48 | $Na_5NiPW_{11}O_{39}$ | |
| 49 | $Na_5NiPW_{11}O_{39}$ | 5 $HAuCl_4$ |
| 50 | $Na_6SiVNbW_{11}O_{39}$ | |
| 51 | $Na_6SiVNbW_{11}O_{39}$ | 5 $HAuCl_4$ |
| 52 | $K_5PMnW_{11}O_{39}$ | |
| 53 | $K_5PMnW_{11}O_{39}$ | 5 $HAuCl_4$ |
| 54 | $K_6SiTiW_{11}O_{40}$ | |
| 55 | $K_6SiTiW_{11}O_{40}$ | 5 $HAuCl_4$ |
| 56 | $K(NH_4)_6RuBW_{11}O_{39}$ | |
| 57 | $K(NH_4)_6RuBW_{11}O_{39}$ | 5 $HAuCl_4$ |
| 58 | $Na_3AsW_{12}O_{40}$ | |
| 59 | $Na_3AsW_{12}O_4$ | 5 $HAuCl_4$ |
| 60 | $K_6FeSiW_{11}O_{39}$ | |
| 61 | $K_6FeSiW_{11}O_{39}$ | 5 $HAuCl_4$ |
| 62 | $K_8NiP_2W_{17}O_{61}$ | |
| 63 | $K_8NiP_2W_{17}O_{61}$ | 5 $HAuCl_4$ |
| 64 | $(Me_4N)_{10}(Co_3SiW_9O_{40}H_6)$ | |
| 65 | $(Me_4N)_{10}(Co_3SiW_9O_{40}H_6)$ | 5 $HAuCl_4$ |
| 66 | $K_{10}Co_4P_2W_{18}O_{68}$ | |
| 67 | $K_{10}Co_4P_2W_{18}O_{68}$ | 5 $HAuCl_4$ |
| 68 | $Na_3V_{10}O_{28}$ | |
| 69 | $Na_3V_{10}O_{28}$ | 5 $HAuCl_4$ |
| 70 | $K_{10}(Mn_4)(PW_9O_{34})_2$ | |
| 71 | $K_{10}(Mn_4)(PW_9O_{34})_2$ | 5 $HAuCl_4$ |
| 72 | $K_{12}Cu_3(W_9PO_{34})_2$ | |
| 73 | $K_{12}Cu_3(W_9PO_{34})_2$ | 5 $HAuCl_4$ |
| 74 | $K_{10}Ni_4P_2W_{17}O_{61}$ | |
| 75 | $K_{10}Ni_4P_2W_{17}O_{61}$ | 5 $HAuCl_4$ |
| 76 | $K_8P_2W_{17}(NbO_2)$ | |
| 77 | $K_8P_2W_{17}(NbO_2)$ | 5 $HAuCl_4$ |
| 78 | $(NH_4)_6P_2FeW_{17}O_{61}$ | |
| 79 | $(NH_4)_6P_2FeW_{17}O_{61}$ | 5 $HAuCl_4$ |
| 80 | $K_8Co(II)P_2W_{17}O_{61}$ | |
| 81 | $K_8Co(II)P_2W_{17}O_{61}$ | 5 $HAuCl_4$ |
| 82 | $K_{12}Pd_3(PW_9O_{34})_2$ | |
| 83 | $K_{12}Pd_3(PW_9O_{34})_2$ | 5 $HAuCl_4$ |
| 84 | $K_7Mn(II)P_2W_{17}O_{61}$ | 5 $HAuCl_4$ |
| 85 | $K_{10}P_2W_{18}Cu_4O_{68}$ | 5 $HAuCl_4$ |
| 86 | $K_8Cu(II)P_2W_{17}O_{61}$ | 5 $HAuCl_4$ |
| 87 | $K_5Si(NbO_2)W_{11}O_{40}$ | 5 $HAuCl_4$ |
| 88 | $K_{12}P_2W_{18}Ni_3O_{68}$ | 5 $HAuCl_4$ |
| 89 | $Na_3H_6Mo_9O_{34}$ | 5 $HAuCl_4$ |
| 90 | $Na_6P_4W_{30}Mn(II)_4O_{112}$ | 5 $HAuCl_4$ |
| 91 | $(NH_4)_6P_2W_{18}O_{62} + 5HAuCl_4$ | 5 $HAuCl_4$ |
| 92 | $(NH_4)_{17}Na(NaSb_9W_{21})O_{86}$ | 5 $HAuCl_4$ |
| 93 | | 5 $Cu(acetate)_2$ |
| 94 | $Na_5PV_2Mo_{10}O_{40}$ | 5 $Cu(acetate)_2$ |
| 95 | | 5 $Co(II)Acac$ |
| 96 | $Na_5PV_2Mo_{10}O_{40}$ | 5 $Co(II)Acac$ |
| 97 | | 5 $Fe(III)Acac$ |
| 98 | $Na_5PV_2Mo_{10}O_{40}$ | 5 $Fe(III)Acac$ |
| 99 | | 5 $MnO_2$ |
| 100 | $Na_5PV_2Mo_{10}O_{40}$ | 5 $MnO_2$ |
| 101 | | 5 $CuCl_2$ |
| 102 | $Na_5PV_2Mo_{10}O_{40}$ | 5 $CuCl_2$ |
| 103 | | 5 $FeCl_3$ |
| 104 | $Na_5PV_2Mo_{10}O_{40}$ | 5 $FeCl_3$ |
| 105 | | 5 $CrCl_3$ |
| 106 | $Na_5PV_2Mo_{10}O_{40}$ | 5 $CrCl_3$ |
| 107 | | 5 $CeCl_3$ |
| 108 | $Na_5PV_2Mo_{10}O_{40}$ | 5 $CeCl_3$ |
| 109 | $Na_9PV_6Mo_6O_{40}$ | 5 $FeCl_3$ |
| 110 | $Na_9PV_6Mo_6O_{40}$ | 5 $CuCl_2$ |
| 111 | $Na_9PV_6Mo_6O_{40}$ | |
| 112 | $K_{12}Pd_3(PW_9O_{36})_2$ | 5 $FeCl_3$ |
| 113 | $K_{12}Pd_3(PW_9O_{36})_2$ | 5 $CuCl_2$ |
| 114 | $K_{12}Pd_3(PW_9O_{36})_2$ | |
| 115 | $Na_5CuPW_{11}O_{39}$ | |
| 116 | $Na_5CuPW_{11}O_{39}$ | 5 $Cr(NO_3)_3$ |
| 117 | | 5 $CrNO_3$ |
| 118 | $Na_5CuPW_{11}O_{39}$ | 5 $Co(NO_3)_2$ |
| 119 | | 5 $Co(NO_3)_2$ |
| 120 | | 5 $Zn(NO_3)_2$ |
| 121 | $Na_5CuPW_{11}O_{39}$ | 5 $Zn(NO_3)_2$ |
| 122 | $Na_5CuPW_{11}O_{39}$ | 5 $Cu(NO_3)_2$ |
| 123 | | 5 $Cu(NO_3)_2$ |
| 124 | $Na_5CuPW_{11}O_{39}$ | 5 $Zn(NO3)3$ |
| 125 | $Na_5CuW_{11}O_{39}$ | 5 $Cu(acetate)_2$ |
| 126 | $Na_5CuW_{11}O_{39}$ | 5 $Fe(acetate)_2$ |
| 127 | $Na_5CuW11O_{39}$ | 5 $MnO_2$ |
| 128 | | 5 $NaNO_3$ |
| 129 | $Li_5PVW_{11}O_{40}$ | 5 $HAuCl_4$ |
| 130 | $AgNO_3$ | |
| 131 | $AgNO_3$ | 5 $HAuCl_4$ |
| 132 | $NaNO_3$ | 5 $HAuCl_4$ |
| 133 | $NaClO_4$ | 5 $HAuCl_4$ |
| 134 | $AgClO_4$ | 5 $HAuCl_4$ |
| 135 | $LiClO_4$ | 5 $HAuCl_4$ |
| 136 | | 5 $(NH_4)_2Ce(NO_3)_6$ |
| 137 | $Na_5PVMo_{11}O_{40}$ | 5 $(NH_4)_2Ce(NO_3)_6$ |
| 138 | $Na_5CuPW_{11}O_{39}$ | 5 $(NH_4)_2Ce(NO_3)_6$ |
| 139 | $Na_5PVMo_{11}O_{40}$ | 5 $CoSO_4$ |
| 140 | $Na_5CuPW_{11}O_{39}$ | 5 $CoSO_4$ |
| 141 | $Na_5PVMo_{11}O_{40}$ | 5 $Ce(SO_4)_2$ |
| 142 | $Na_5CuPW_{11}O_{39}$ | 5 $Ce(SO_4)_2$ |
| 143 | $Na_5PVMo_{11}O_{40}$ | 5 $H_2PtCl_6$ |
| 144 | $Na_5CuPW11O_{39}$ | 5 $H_2PtCl_6$ |
| 145 | $Na_5PVMo_{11}O_{40}$ | 5 $Pd(NO_3)_2$ |
| 146 | $Na_5CuPW_{11}O_{39}$ | 5 $Pd(NO_3)_2$ |
| 147 | $Na_5PVMo_{11}O_{40}$ | 5 $RhCl_3$ |
| 148 | $Na_5CuPW_{11}O_{39}$ | 5 $RhCl_3$ |
| 149 | $Na_5PVMo_{11}O_{40}$ | 5 $ReO_2$ |
| 150 | $Na_5CuPW_{11}O_{39}$ | 5 $ReO_2$ |

Figure 1:
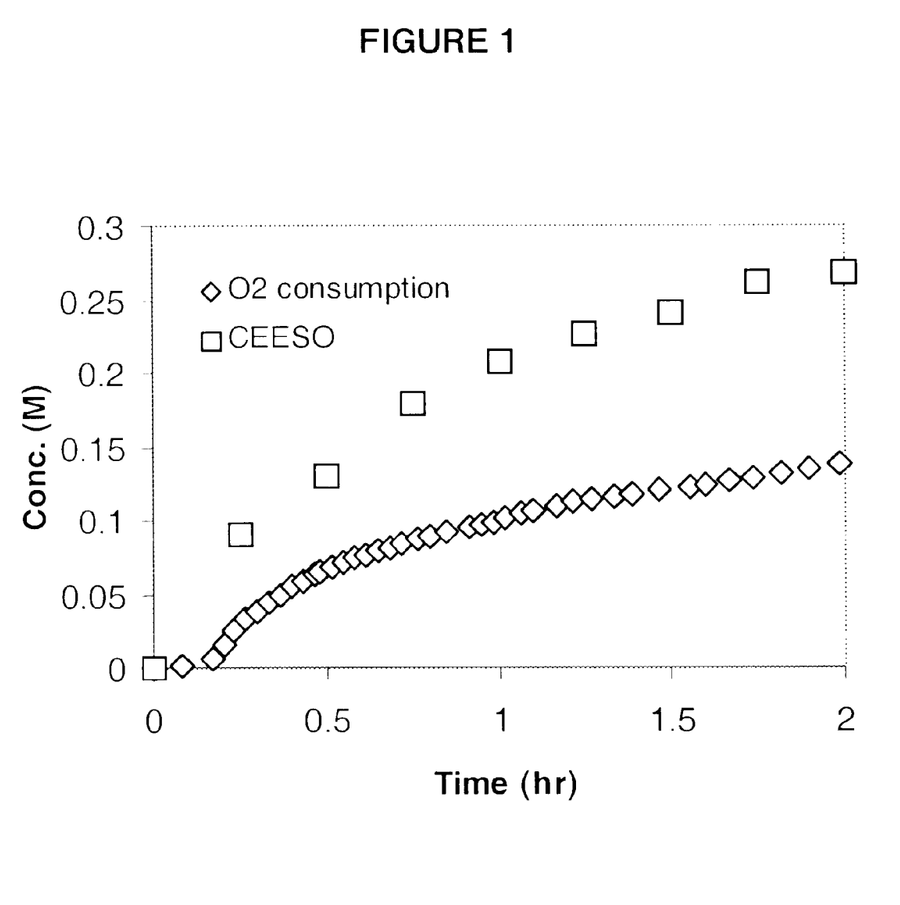
FIG. 1 shows the consumption of oxygen and formation of CEESO as a function of time.

Example 11
Oxidation of CEES to CEESO by Metal Compounded (Non-POM)
(a) Determining the Stoichiometry of $O_2$ in the Catalytic Oxidation of CEES A schlenk flask fitted with septum was attached to a manometer and purged with $O_2$. To the flask containing 1.36 mL of acetonitrile, solutions (all in acetonitrile) of 0.002 mL of $(NEt_4)AuCl_2$ ($5.0 \times 10^{-6}$ mol), 0.188 mL of $AgClO_4$ solution ($10 \times 10^{-5}$ mol), 0.094 mL $NBu_4NO_3$ solution ($5.0 \times 10^{-6}$ mol), 0.166 mL 1,3-dichlorobenzene ($7.5 \times 10^{-4}$ mol) (internal standard for GC), and 0.084 mL CEES ($3.8 \times 10^{-4}$ mol) were added. The consumption of $O_2$ was recorded, and aliquots were periodically taken and injected into the GC. The stoichiometry of $O_2$ consumption was established using a manometer to determine the amount of $O_2$ consumed while simultaneously monitoring CEESO formation with a gas chromatography. FIG. 1 reveals that one equivalent of the CEESO formed corresponds of 0.5 equivalents of $O_2$.

(b) Cream Formulation Reactions

Experiments were performed using the perfluorinated oil, Galden DO2, and Fomblin perfluorinated polyether oil as "solvent," both of which are components of the cream. Samples were prepared by adding components together, dissolving in a minimal amount of acetonitrile, stirring for 10 minutes, and then removing the solvent by vacuum.

In all cases where $(NEt_4)AuCl_2$ was used as the gold compound, $1.25 \times 10^{-5}$ mol of the gold compound was used. The other components which were varied in quantities were $NBu_4NO_3$ ($1.25 \times 10^{-5}$–$1.25 \times 10^{-4}$ mol), and a $CuSO_4$ ($1.25 \times 10^{-5}$–$1.25 \times 10^{-4}$ mol) (Table 9). The gold, copper, and/or nitrate salts were admixed in acetonitrile, then the solvent was removed by vacuum. After the mixture was dried by vacuum in a Schlenk flask, the flask is attached to the manometer and the apparatus is purged with $O_2$. After purging, 7.0 mL of the perfluorinated fluid was added to the flask. The system was equilibrated to atmospheric pressure then sealed from any external atmosphere. Through the septum 0.05 mL ($4.2 \times 10^{-4}$ mol) of CEES was added and the system was monitored for $O_2$ consumption. Table 9 shows CEESO formation after 1hour using various cream formulations (7.0 mL Galden DO2).

TABLE 9[a]

| [Au] | [NO$_3$] | [Cu$^{+2}$] | [CEESO formed] |
|------|----------|-------------|----------------|
| 0    | 1.25     | 1.25        | 3.62           |
| 1.25 | 1.25     | 1.25        | 5.80           |
| 0    | 2.50     | 2.50        | 5.00           |
| 1.25 | 2.50     | 2.50        | 8.06           |
| 0    | 5.00     | 7.25        | 8.06           |
| 1.25 | 5.00     | 7.25        | 16.20          |
| 0    | 10.00    | 12.50       | 10.60          |
| 1.25 | 10.00    | 12.50       | 18.70          |

[a]All concentrations expressed in $10^{-5}$ mol.

Another experiment was performed using Fomblin as the "solvent." In this case, 1.0 mL Fomblin, 0.005 g of $(NEt_4)AuCl_2$ ($1.25 \times 10^{-5}$ mol), was admixed in with varying amounts of $CuSO_4$, $MnSO_4$, $VOSO_4$, $Ti(SO_4)_2$, $Fe_2(SO_4)_3$, $NiSO_4$, $ZnSO_4$, $Cr(SO_4)_3$, $MgSO_4$, $CoSO_4$, $Pd(NO_3)_4$, $Na_2SO_3$, and/or $NBu_4NO_3$. The catalyst was prepared and the experiment was performed using the same method as earlier reported. Table 10 reveals CEESO formation in PFPE Surfactant (1.0 mL Fomblin) using various metals compounds. The metal compounds are abbreviated for simplicity sake. For example, metal compound 1Au/1Cu(II)/1NO$_3$ was prepared by mixing one equivalent each $(NEt_4)AuCl_2$, $CuSO_4$, and $NBu_4NO_3$.

TABLE 10

| Metal Compound | Turnovers of CEESO after 10 min (based on Au) |
|----------------|-----------------------------------------------|
| 1Au/1Cu(II)/1NO$_3$ | 17 |
| 1Au/2Cu(II)/1NO$_3$ | 28 |
| 1Au/1Cu(II)/2NO$_3$ | 115 |

TABLE 10-continued

| Metal Compound | Turnovers of CEESO after 10 min (based on Au) |
|----------------|-----------------------------------------------|
| 1Au/2Cu(II)/2NO$_3$ | 155 |
| 1Au/1Cu(II)/3NO$_3$ | 155 |
| 1Au/1Fe(III)/3NO$_3$ | 142 |
| 1Au/2Mn(II)/3NO$_3$ | 164 |
| 1Au/2Ti(IV)/3NO$_3$ | 142 |
| 1Au/2Co(II)/3NO$_3$ | 177 |
| 1Au/4NO$_3$ | 185 |
| 1Au/2Cu(II)/3NO$_3$ | 181 |
| 1Au/2Cu(II)/4NO$_3$ | 195 |
| 1Au/3Cu(II)/3NO$_3$ | 165 |
| 2Cu(II)/3NO$_3$ | 28 |
| 1Au/3NO$_3$ | 150 |
| 1Fe(III)/3NO$_3$ | 19 |
| 1Au/2V(IV)/3NO$_3$ | 160 |
| 1Au/2Ni(II)/3NO$_3$ | 140 |
| 1Au/2Ag(II)/3NO$_3$ | 184 |

Figure 2:
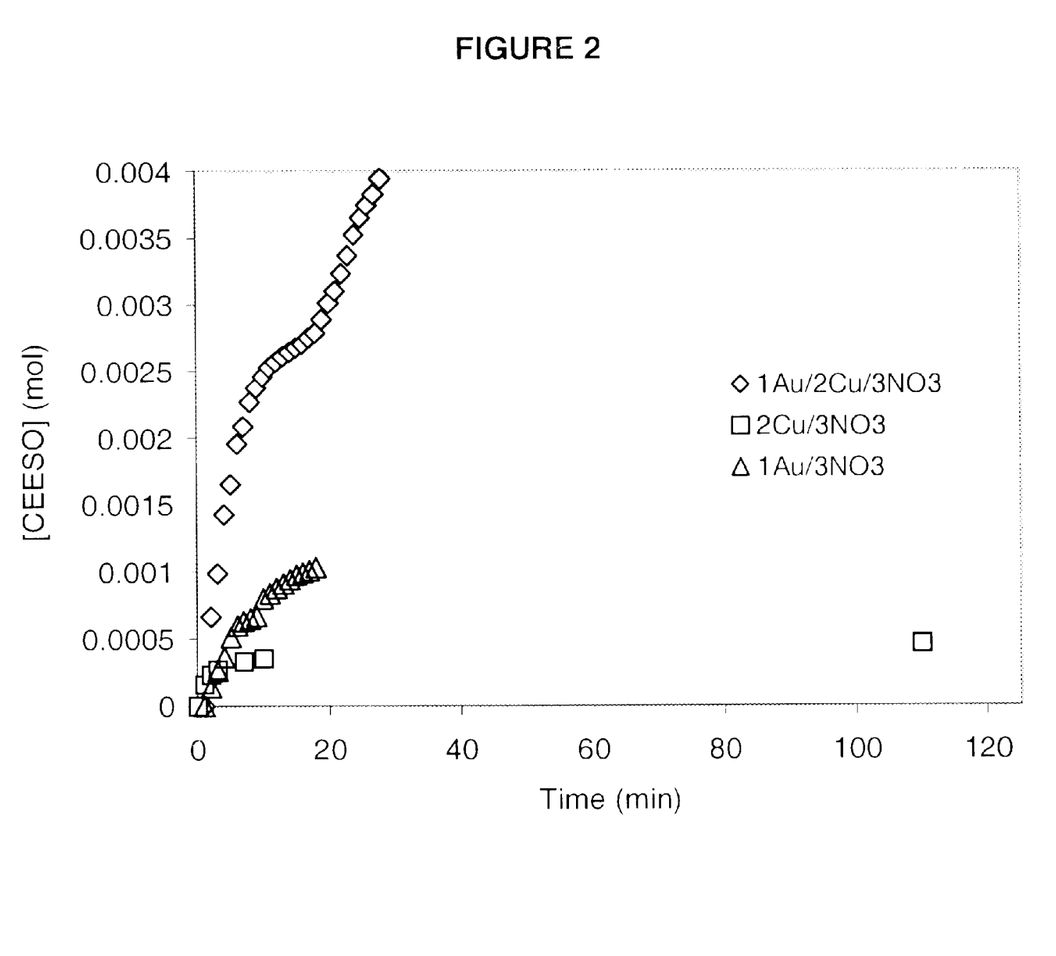
FIG. 2 shows CEESO formation as a function of time using $1Au/2Cu/3NO_3$; $2Cu/3NO_3$; and $1Au/3NO_3$.

FIG. 2 shows CEESO formation as a function of time for 1Au/2Cu(II)/3NO$_3$, 2Cu(II)/3NO$_3$, 1Au/3NO$_3$. From the data in Table 10 and FIG. 2, it is clear that there was a synergistic effect when certain redox active metals were added to the Au/NO$_3$ system. For example, one of the most active systems, 1Au/2Cu(II)/3NO$_3$ was 3.8 and 6.5 times more effective after 10 minutes of reaction time than when only 2 of the components were used, 1Au/3NO$_3$ and 2Cu(II)/3NO$_3$ respectively. Also, FIG. 2 shows that inhibition was less pronounced in the three components systems. Another important aspect of this system is that the oxidation terminates to the sulfoxide without continued oxidation to yield the sulfone. This is important as it relates to toxicity issues as it is believed that the sulfoxide of mustard gas is significantly less toxic than the corresponding sulfone.

Example 12

Synthesis, Characterization, and Reactivity of Organo-Modified POMs (a) Synthesis of $Ag_2[V_6O_{13}((OCH_2)_3CCH_3)_2]$(Ag Me cap) $Na_2[V_6O_{13}((OCH_2)_3CCH_3)_2]$(Na Me cap, 0.480 g) was dissolved in ~4 mL of distilled water. This was filtered over a medium fritted funnel to remove any undissolved POM. To the dark red-orange solution was added $AgNO_3$ (0.215 g) with stirring. An orange-red precipitated immediately. The crude product was separated by suction filtration over a medium frit, washed with room temperature water and ether. The product was dried over night in vacuo. Crystals were grown by diffusing ether into an acetonitrile solution of the product at room temperature. $^{51}$V NMR (0.04 g dissolved in 2.0 mL of MeCN) –449.232 ppm (singlet). Solid-state IR (KBr pellet, 1400–400 cm$^{-1}$) 1452.11 (m), 1390.47 (w), 1200.43 (w), 1128.53 (m), 1015.5 (s), 953.9 (vs), 820.36 (sh), 794.68 (s), 712.5 (s), 614.91 (sh), 584.09 (m), 424.87 (s).

(b) Synthesis of $Co[V_6O_{13}((OCH_2)_3CCH_3)_2]$(Co Me cap)

The same procedure for the synthesis of $Ag_2[V_6O_{13}((OCH_2)_3CCH_3)_2]$ was followed, excepted $CoCl_2$ was added to form the Co salt of the POM. Crystals were grown from diffusing isopropyl alcohol into a MeCN solution of crude product. $^{51}$V NMR (0.04 g dissolved in 2.0 mL of MeCN) –500.3 ppm (singlet). Solid-state IR (KBr pellet, 1400–400 cm$^{-1}$) 1452.11 (m), 1390.47 (w), 1200.43 (w), 1128.53 (m), 1015.5 (s), 935.9 (vs), 820.36 (sh), 794.68 (s), 712.5 (s), 614.91 (sh), 584.09 (m), 424.87 (s).

(c) Reactivity of Organo-Modified POMs

Table 11 lists the oxidation of tetrahydrothiophene (THT) by t-butlhydroperoxide (TBHP) catalyzed by the transition metal salts of Me-capped $V_6O_{13}$. The oxidations were performed by dissolving the particular salt acetonitrile to give lightly colored orange-yellow solutions. The solutions were placed in 24-mL vials fitted with PTFE septa. THT and TBHP were then syringed in and the reactions were monitored by quantitative GC. Reactions were stirred at room temperature.

TABLE 11

Room Temperature Oxidation of THT to THTO by TBHP Catalyzed by Transition Metal Salts of Me Capped $V_6O_{13}$ after 48 Hours.

| Catalyst | Mols of catalyst, $\times 10^{-6}$ | Mols of THTO, $\times 10^{-5}$ | Turnover number[b] |
|---|---|---|---|
| Na Me cap | 1.76 | 6.03 | 34.3 |
| Ag Me cap | 1.87 | 5.59 | 30.0 |
| Co Me cap | 1.61 | 6.33 | 39.3 |
| $AgNO_3$ | 14.1 | 1.06 | 0.754 |
| $CoCl_3$ | 39.5 | 2.25 | 0.570 |
| blank[a] | NA | 0 | 0 |

[a]blank reaction: 3.0 mL of MeCN, 0.018 mL of THT, 0.010 mL of internal reference.
[b]Turnover number = (mols of THTO)/(mols of catalyst) × 100

Throughout this application, various publications are referenced. The disclosures of these publications in their entireties are hereby incorporated by reference into this application in order to more fully describe the state of the art to which this invention pertains.

It with be apparent to those skilled in the art that various modifications and variations can be made in the present invention without departing from the scope or spirit of the invention. Other embodiments of the will be apparent to those skilled in the art from consideration of the specification and practice of the invention disclosed herein. It is intended that the specification and examples be considered as exemplary only.

What is claimed is:

1. A polyoxometalate topical composition for removing a contaminant from an environment, comprising a topically acceptable pharmaceutical carrier and at least one polyoxometalate, said polyoxometalate having the formula $[YV_xZ_{12-x}O_{40}][A]$, wherein (a) Y is phosphorus, silicon, or aluminum; Z is tungsten or molybdenum; x is from 1 to 6, and A is a counterion, with the proviso that the polyoxometalate is not $H_5PV_2Mo_{10}O_{40}$ or $H_6PV_3Mo_9O_{40}$, and (b) said carrier is suitable for application of a thin layer of the composition on the skin of a human.

2. The composition of claim 1, wherein the topical carrier comprises a perfluorinated polymer.

3. The composition of claim 1, wherein the topical carrier comprises a perfluorinated polymer and at least one unfluorinated polymer.

4. The composition of claim 1, wherein the topical carrier comprises a perfluoropolyether.

5. The composition of claim 1, wherein the topical carrier comprises a perfluoropolyether and at least one unfluorinated polyether.

6. The composition of claim 1, wherein the polyoxometalate is from 0.01 to 95% by weight of the polyoxometalate topical composition.

7. The composition of claim 1, wherein the topical carrier is a perfluoropolyether and A is silver.

8. A method for removing a contaminant from an environment, composition contacting the polyoxometalate topical composition of claim 1 with the environment containing the contaminant for a sufficient time to remove the contaminant from the environment.

9. The method of claim 8, wherein the environment comprises a gas phase.

10. The method of claim 8, wherein the environment comprises a liquid phase.

11. The method of claim 8, wherein the contaminant comprises a chemical warfare agent.

12. The method of claim 8, wherein the contaminant comprises an aldehyde, an aliphatic nitrogen compound, a sulfur compound, an aliphatic oxgenated compound, a halogenated compound, an organophosphate compound, a phosphonothioate compound, a phosphorothioate compound, an arsenic compound, a chloroethyl-amine compound, a phosgene compound, a cyanic compound, or a combination thereof.

13. The method of claim 8, wherein the contaminant comprises acetaldehyde, methyl mercaptan, ammonia, hydrogen sulfide, methyl sulfide, diethyl sulfide, diethyl disulfide, dimethyl sulfide, dimethyl disulfide, trimethylamine, styrene, propionic acid, n-butyric acid, n-valeric acid, iso-valeric acid, pyridine, formaldehyde, 2-chloroethyl ethyl sulfide, carbon monoxide, or a combination thereof.

14. The method of claim 8, wherein when the environment is a gas phase, the contaminant is removed from the gas phase at from −50° C. to 250° C. and the contaminant from gas phase has a partial pressure of from 0.1 ppb to 30 atm.

15. The method of claim 8, wherein when the environment is a gas phase, the contaminant is removed from the gas phase at from 0° C. to 105° C. and the contaminant from the gas phase has a partial pressure of 1 atm.

16. The composition of claim 1, wherein the polyoxometalate includes $Na_5PcuW_{11}O_{39}$.

17. The composition of claim 1, wherein the polyoxometalate includes $Na_5PV_2Mo_{10}O_{40}$.

* * * * *

UNITED STATES PATENT AND TRADEMARK OFFICE
Certificate

Patent No. 6,723,349 B1                                                      Patented: April 20, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Craig L. Hill, Atlanta, GA (US); Ling Xu, Atlanta, GA (US); Jeffrey T. Rhule, Franklin, OH (US); Eric A. Boring, Atlanta, GA (US); Ernest H. Braue, Jr., Whiteford, MD (US); and Stephen T. Hobson, Belcamp, MD (US).

Signed and Sealed this Nineteenth Day of May 2009.

<div style="text-align: right;">
JOHANN RICHTER<br>
*Supervisory Patent Examiner*<br>
Art Unit 1616
</div>